(12) United States Patent
Churchill et al.

(10) Patent No.: US 12,102,545 B2
(45) Date of Patent: *Oct. 1, 2024

(54) IMPLANT DELIVERY DEVICE

(71) Applicant: EMBODY, INC., Norfolk, VA (US)

(72) Inventors: R. Sean Churchill, Grand Rapids, MI (US); Robert J. Ball, West Olive, MI (US); Douglas Snell, Grand Rapids, MI (US); Isaac Running, Grand Rapids, MI (US); Christopher K. Jones, Colorado Springs, CO (US); Brandon Bryant, Vienna, VA (US)

(73) Assignee: Embody, Inc., Norfolk, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/510,187

(22) Filed: Nov. 15, 2023

(65) Prior Publication Data

US 2024/0082017 A1     Mar. 14, 2024

Related U.S. Application Data

(63) Continuation of application No. 17/682,748, filed on Feb. 28, 2022, now Pat. No. 11,850,167, which is a
(Continued)

(51) Int. Cl.
*A61F 2/46*     (2006.01)
*A61B 17/34*     (2006.01)

(52) U.S. Cl.
CPC ........ *A61F 2/4601* (2013.01); *A61B 17/3423* (2013.01); *A61B 17/3462* (2013.01); *A61B 17/3498* (2013.01)

(58) Field of Classification Search
CPC .......................... A61F 2/4601; A61B 17/3462
See application file for complete search history.

(56) References Cited

U.S. PATENT DOCUMENTS 5,195,542 A    3/1993   Gazielly et al.
5,318,589 A    6/1994   Lichtman
(Continued)

FOREIGN PATENT DOCUMENTS

AU     2021220863 B2    3/2024
CA       3170125 A1    8/2021
(Continued)

OTHER PUBLICATIONS

"U.S. Appl. No. 17/174,011, Examiner Interview Summary mailed Oct. 7, 2021", 2 pgs.
(Continued)

*Primary Examiner* — Si Ming Ku
(74) *Attorney, Agent, or Firm* — SCHWEGMAN LUNDBERG & WOESSNER, P.A.

(57) ABSTRACT

An implant delivery device may include an implant holding portion proximate the distal end, the implant holding portion being configured to retain a sheet-like implant during implantation of the implant. In addition, the implant holding portion may be configured to receive the implant with a fixed implant supporting flange member configured to support the implant on one side, and a movable implant supporting flange member. The movable implant supporting flange member may be configured to be slidable between a distal position and a proximal position, wherein, in the distal position, the movable implant supporting flange member and secures the implant against the fixed implant supporting flange member, and in the proximal position, the movable implant supporting flange member is withdrawn from the distal end of the implant delivery device, thus enabling release of the implant.

18 Claims, 20 Drawing Sheets

Related U.S. Application Data continuation of application No. 17/174,011, filed on Feb. 11, 2021, now Pat. No. 11,259,939.

(60) Provisional application No. 62/972,775, filed on Feb. 11, 2020.

(56) References Cited

U.S. PATENT DOCUMENTS

| | | |
|---|---|---|
| 5,441,508 A | 8/1995 | Gazielly et al. |
| 6,179,872 B1 | 1/2001 | Bell |
| 6,755,863 B2 | 6/2004 | Ferree |
| 6,852,330 B2 | 2/2005 | Bowman et al. |
| 7,153,312 B1 | 12/2006 | Torrie et al. |
| 7,559,941 B2 | 7/2009 | Zannis et al. |
| 7,601,165 B2 | 10/2009 | Stone |
| 7,658,751 B2 | 2/2010 | Stone et al. |
| 7,749,250 B2 | 7/2010 | Stone et al. |
| 7,803,395 B2 | 9/2010 | Datta et al. |
| 7,819,918 B2 | 10/2010 | Malaviya et al. |
| 7,887,551 B2 | 2/2011 | Bojarski et al. |
| 7,909,851 B2 | 3/2011 | Stone et al. |
| 7,963,972 B2 | 6/2011 | Foerster et al. |
| 8,080,260 B2 | 12/2011 | Derwin et al. |
| 8,084,428 B2 | 12/2011 | Spector et al. |
| 8,088,130 B2 | 1/2012 | Kaiser et al. |
| 8,092,529 B2 | 1/2012 | Malaviya et al. |
| 8,118,836 B2 | 2/2012 | Denham et al. |
| 8,128,658 B2 | 3/2012 | Kaiser et al. |
| 8,361,113 B2 | 1/2013 | Stone et al. |
| 8,585,773 B1 | 11/2013 | Kucklick |
| 8,668,718 B2 | 3/2014 | Euteneuer et al. |
| 8,753,359 B2 | 6/2014 | Levin et al. |
| 8,763,878 B2 | 7/2014 | Euteneuer et al. |
| 8,821,507 B2 | 9/2014 | Axelson, Jr. et al. |
| 8,821,536 B2 | 9/2014 | Euteneuer et al. |
| 8,821,537 B2 | 9/2014 | Euteneuer et al. |
| 8,840,642 B2 | 9/2014 | Euteneuer et al. |
| 8,864,780 B2 | 10/2014 | Euteneuer et al. |
| 8,888,811 B2 | 11/2014 | Levin et al. |
| 8,906,045 B2 | 12/2014 | Levin et al. |
| 8,920,464 B2 | 12/2014 | Euteneuer et al. |
| 9,005,224 B2 | 4/2015 | Euteneuer et al. |
| 9,027,819 B2 | 5/2015 | Euteneuer et al. |
| 9,033,201 B2 | 5/2015 | Euteneuer |
| 9,095,337 B2 | 8/2015 | Euteneuer et al. |
| 9,101,460 B2 | 8/2015 | Euteneuer et al. |
| 9,107,726 B2 | 8/2015 | Levin et al. |
| 9,113,977 B2 | 8/2015 | Euteneuer et al. |
| 9,179,910 B2 | 11/2015 | Euteneuer et al. |
| 9,179,961 B2 | 11/2015 | Euteneuer et al. |
| 9,198,750 B2 | 12/2015 | Van Kampen et al. |
| 9,198,751 B2 | 12/2015 | Euteneuer et al. |
| 9,204,940 B2 | 12/2015 | Euteneuer et al. |
| 9,259,220 B2 | 2/2016 | Euteneuer et al. |
| 9,314,331 B2 | 4/2016 | Euteneuer et al. |
| 9,393,002 B2 | 7/2016 | Iceman et al. |
| 9,393,103 B2 | 7/2016 | Van Kampen et al. |
| 9,393,104 B2 | 7/2016 | Kampen et al. |
| 9,642,891 B2 | 5/2017 | Hart et al. |
| 9,655,709 B2 | 5/2017 | Kelly et al. |
| 9,675,346 B2 | 6/2017 | Euteneuer et al. |
| 9,743,970 B2 | 8/2017 | Euteneuer et al. |
| 9,878,141 B2 | 1/2018 | Kucklick |
| 9,931,119 B2 | 4/2018 | Euteneuer et al. |
| 9,993,247 B2 | 6/2018 | Euteneuer |
| 10,085,785 B2 | 10/2018 | Euteneuer et al. |
| 10,105,210 B2 | 10/2018 | Van Kampen et al. |
| 10,123,866 B2 | 11/2018 | Van Kampen et al. |
| 10,172,703 B2 | 1/2019 | Adams et al. |
| 10,195,016 B2 | 2/2019 | Euteneuer et al. |
| 10,226,269 B2 | 3/2019 | Weihe |
| 10,226,325 B2 | 3/2019 | Euteneuer et al. |
| 10,245,138 B2 | 4/2019 | Euteneuer et al. |
| 10,258,459 B2 | 4/2019 | Zenz-Olson |
| 10,265,156 B2 | 4/2019 | Van Kampen |
| 10,278,801 B2 | 5/2019 | Kucklick |
| 10,307,238 B2 | 6/2019 | Kucklick |
| 10,314,689 B2 | 6/2019 | Zenz-Olson et al. |
| 10,376,352 B2 | 8/2019 | Kelly et al. |
| 10,413,397 B2 | 9/2019 | Euteneuer et al. |
| 10,426,464 B2 | 10/2019 | Euteneuer et al. |
| 10,449,031 B2 | 10/2019 | Euteneuer et al. |
| 10,568,622 B2 | 2/2020 | Euteneuer et al. |
| 10,653,415 B2 | 5/2020 | Euteneuer et al. |
| 10,675,016 B2 | 6/2020 | Coleman |
| 10,695,155 B2 | 6/2020 | Levin et al. |
| 10,765,423 B2 | 9/2020 | Coleman |
| 10,806,565 B2 | 10/2020 | Euteneuer et al. |
| 10,813,742 B2 | 10/2020 | Adams et al. |
| 10,820,981 B2 | 11/2020 | Ravenscroft et al. |
| 10,835,235 B2 | 11/2020 | Coleman |
| 10,835,368 B2 | 11/2020 | Zenz-Olson et al. |
| 10,864,072 B2 | 12/2020 | Van Kampen et al. |
| 10,874,503 B2 | 12/2020 | Zenz-Olson et al. |
| 11,259,939 B2 | 3/2022 | Churchill et al. |
| 11,850,167 B2 | 12/2023 | Churchill et al. |
| 2002/0127265 A1 | 9/2002 | Bowman et al. |
| 2004/0267304 A1* | 12/2004 | Zannis ............... A61F 2/4618 606/206 |
| 2005/0113938 A1 | 5/2005 | Jamiolkowski et al. |
| 2006/0029633 A1 | 2/2006 | Kaiser et al. |
| 2006/0247641 A1 | 11/2006 | Re et al. |
| 2007/0156174 A1 | 7/2007 | Kaiser et al. |
| 2007/0190108 A1 | 8/2007 | Datta et al. |
| 2007/0288023 A1 | 12/2007 | Pellegrino et al. |
| 2008/0051809 A1 | 2/2008 | Verhelst et al. |
| 2009/0156986 A1 | 6/2009 | Trenhaile |
| 2009/0156997 A1 | 6/2009 | Trenhaile |
| 2010/0191332 A1 | 7/2010 | Euteneuer et al. |
| 2010/0312357 A1 | 12/2010 | Levin et al. |
| 2012/0209401 A1 | 8/2012 | Euteneuer |
| 2012/0265219 A1 | 10/2012 | Rushdy et al. |
| 2013/0172997 A1* | 7/2013 | Euteneuer ............ A61B 90/39 623/13.11 |
| 2013/0184716 A1 | 7/2013 | Euteneuer et al. |
| 2014/0081285 A1* | 3/2014 | Kucklick ............ A61B 17/34 606/108 |
| 2015/0327975 A1 | 11/2015 | Euteneuer et al. |
| 2016/0058535 A1 | 3/2016 | Euteneuer et al. |
| 2016/0345991 A1 | 12/2016 | Weihe |
| 2017/0202920 A1 | 7/2017 | Hart et al. |
| 2018/0256162 A1 | 9/2018 | Euteneuer |
| 2018/0360914 A1 | 12/2018 | Hart et al. |
| 2019/0015145 A1 | 1/2019 | Euteneuer et al. |
| 2019/0029802 A1 | 1/2019 | Van Kampen et al. |
| 2019/0038395 A1 | 2/2019 | Van Kampen |
| 2019/0110885 A1 | 4/2019 | Zenz-Olson et al. |
| 2019/0175328 A1 | 6/2019 | Zenz-Olson et al. |
| 2019/0209287 A1 | 7/2019 | Zenz-Olson |
| 2019/0254802 A1 | 8/2019 | Kucklick |
| 2019/0274675 A1 | 9/2019 | Coleman |
| 2019/0274814 A1 | 9/2019 | Euteneuer et al. |
| 2019/0282352 A1 | 9/2019 | Kucklick |
| 2019/0350608 A1 | 11/2019 | Kucklick |
| 2019/0388215 A1 | 12/2019 | Euteneuer et al. |
| 2020/0000462 A1 | 1/2020 | Euteneuer et al. |
| 2020/0170780 A1 | 6/2020 | Euteneuer et al. |
| 2020/0197003 A1 | 6/2020 | Euteneuer et al. |
| 2020/0237499 A1 | 7/2020 | Zenz-Olson et al. |
| 2021/0275322 A1 | 9/2021 | Churchill et al. |
| 2022/0249250 A1 | 8/2022 | Churchill et al. |

FOREIGN PATENT DOCUMENTS

| | | |
|---|---|---|
| CN | 115297805 A | 11/2022 |
| EP | 4103106 A1 | 12/2022 |
| FR | 2800595 B1 | 1/2002 |
| JP | H0857056 A | 3/1996 |
| JP | 2016517330 A | 6/2016 |
| JP | 2017513655 A | 6/2017 |
| JP | 2023514192 A | 4/2023 |

(56) References Cited

FOREIGN PATENT DOCUMENTS

| WO | WO-2007056297 A2 | 5/2007 |
| WO | WO-2021163337 A1 | 8/2021 |

OTHER PUBLICATIONS

"U.S. Appl. No. 17/174,011, Non Final Office Action mailed Jun. 29, 2021", 10 pgs.

"U.S. Appl. No. 17/174,011, Notice of Allowance mailed Oct. 20, 2021", 9 pgs.

"U.S. Appl. No. 17/174,011, Response filed Sep. 29, 2021 to Non Final Office Action mailed Jun. 29, 2021", 11 pgs.

"U.S. Appl. No. 17/174,011, Supplemental Amendment filed Oct. 6, 2021", 9 pgs.

"U.S. Appl. No. 17/682,748, Non Final Office Action mailed Apr. 4, 2023", 12 pgs.

"U.S. Appl. No. 17/682,748, Notice of Allowance mailed Aug. 22, 2023", 8 pgs.

"U.S. Appl. No. 17/682,748, Response filed May 15, 2023 to Non Final Office Action mailed Apr. 4, 2023", 9 pgs.

"Australian Application Serial No. 2021220863, First Examination Report mailed Aug. 21, 2023", 4 pgs.

"Canadian Application Serial No. 3,170,125, Examiners Rule 86(2) Report mailed Sep. 16, 2023", 6 pgs.

"International Application Serial No. PCT/US2021/017674, International Preliminary Report on Patentability mailed Aug. 25, 2022", 7 pgs.

"International Application Serial No. PCT/US2021/017674, International Search Report mailed May 6, 2021", 2 pgs.

"International Application Serial No. PCT/US2021/017674, Written Opinion mailed May 6, 2021", 6 pgs.

"Japanese Application Serial No. 2022-548553, Written Amendment filed Dec. 1, 2022", w/ English Translation, 8 pgs.

"Rotator Cuff Failure, UW Orthopaedics and Sports Medicine, Seattle", [Online]. Retrieved from the Internet: <URL: https://orthop.washington.edu/patient-care/articles/shoulder/rotator-cuff-failure.Html>, (Jan. 25, 2005), 11 pgs.

"Australian Application Serial No. 2021220863, Response filed Nov. 27, 2023 to First Examination Report mailed Aug. 21, 2023", 13 pgs.

"Canadian Application Serial No. 3,170,125, Response filed Feb. 9, 2024 to Examiners Rule 86(2) Report mailed Oct. 16, 2023", 17 pgs.

"European Application Serial No. 21753955.0, Extended European Search Report mailed Feb. 14, 2024", 7 pgs.

"Japanese Application Serial No. 2022-548553, Decision of Rejection mailed Feb. 29, 2024", w/ English Translation, 6 pgs.

"Japanese Application Serial No. 2022-548553, Notification of Reasons for Rejection mailed Nov. 2, 2023", W/English Translation, 9 pgs.

"Japanese Application Serial No. 2022-548553, Response filed Jan. 16, 2024 to Notification of Reasons for Rejection mailed Nov. 2, 2023", w/ current English claims, 10 pgs.

\* cited by examiner

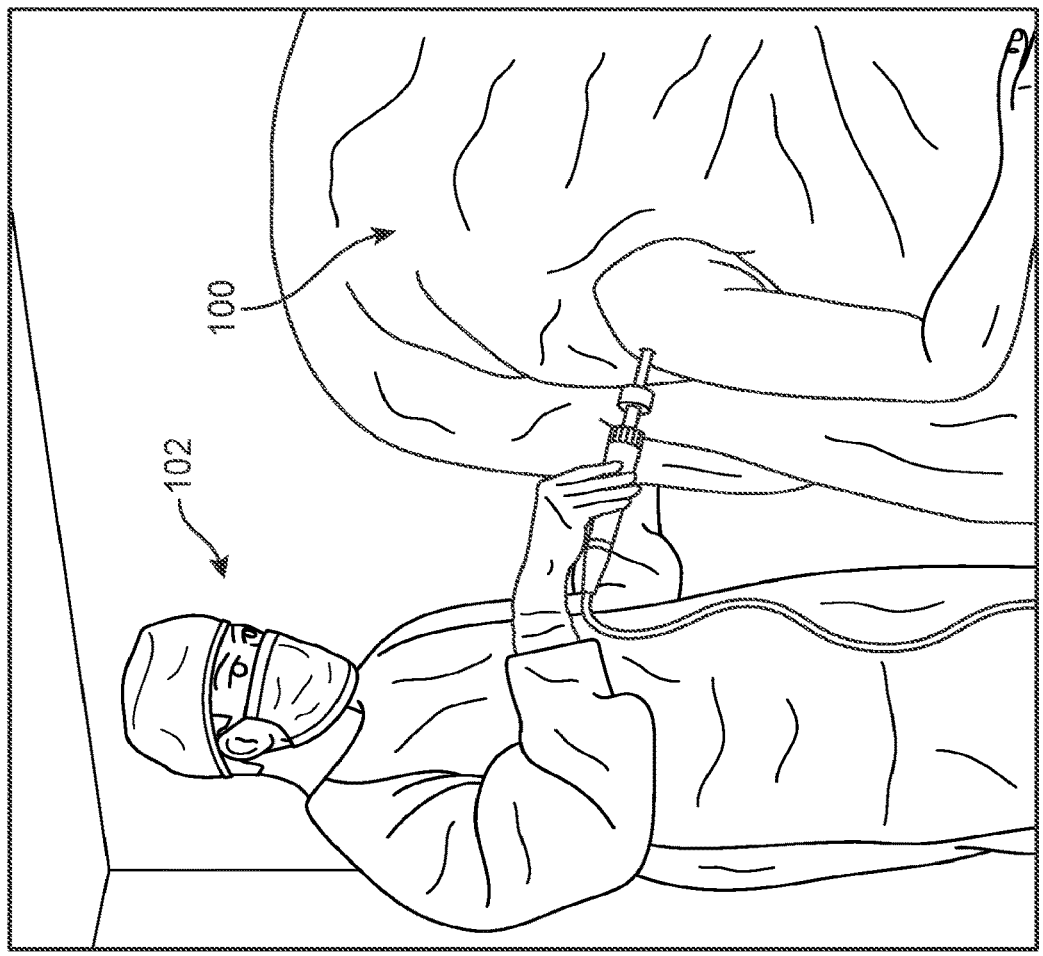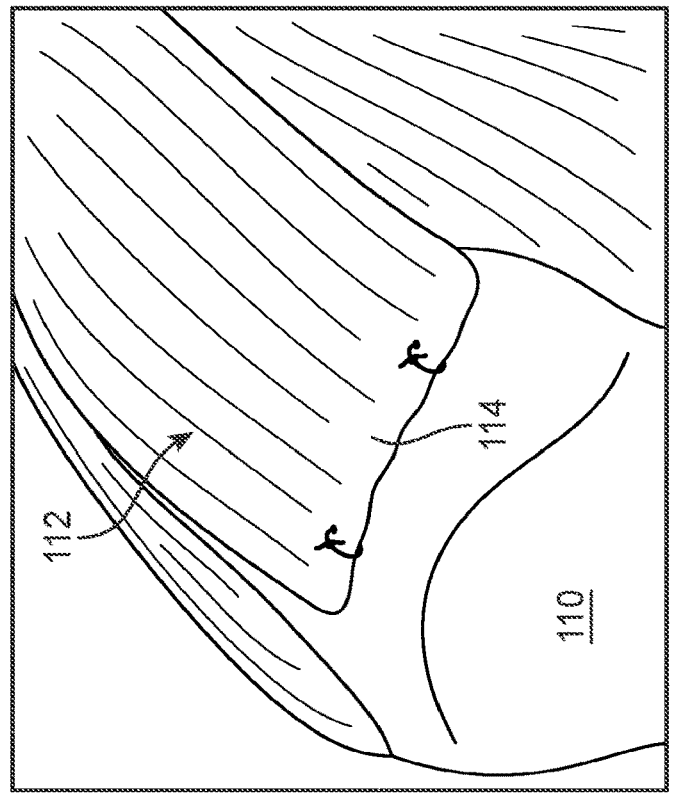
FIG. 1

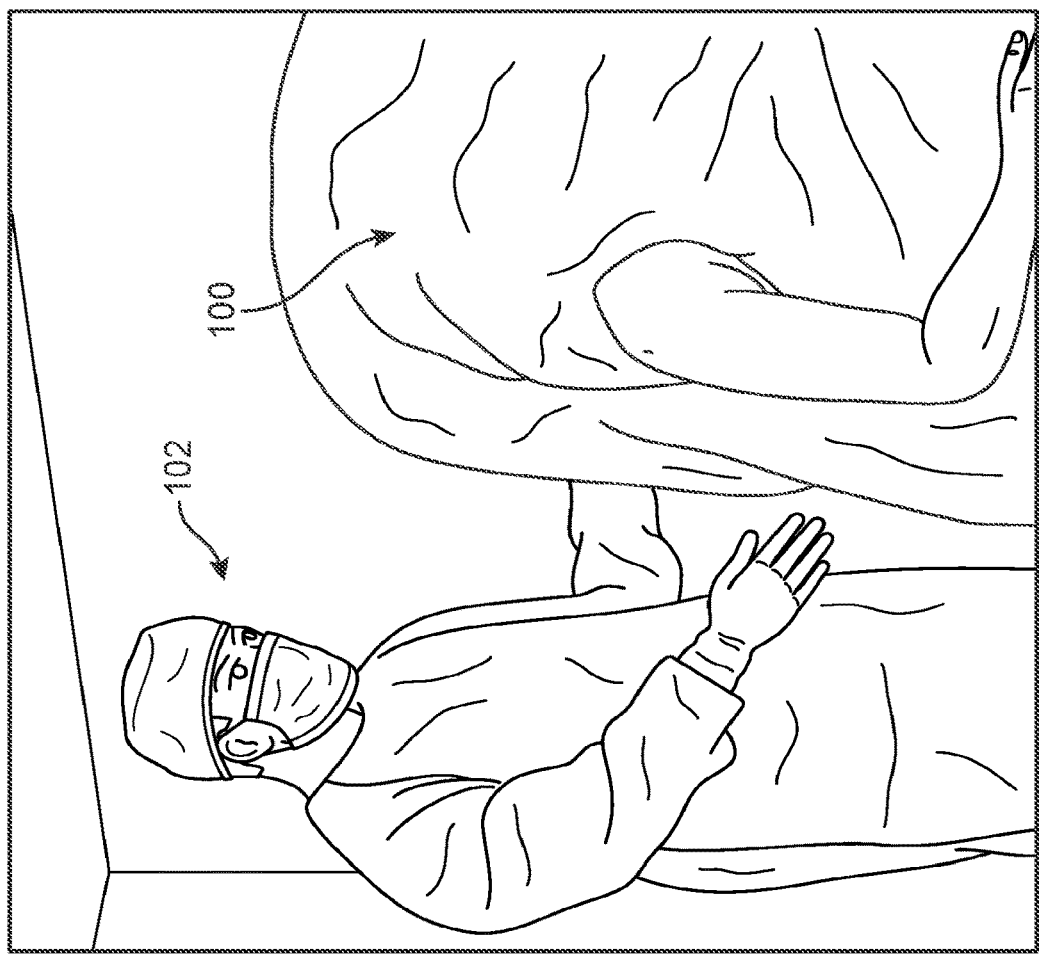
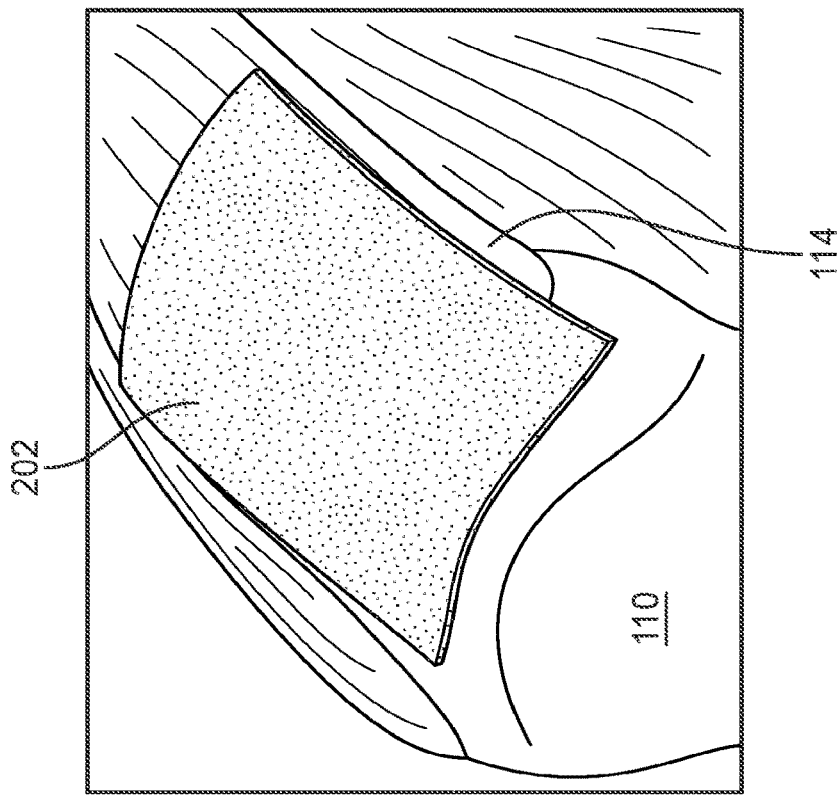
FIG. 2

IMPLANT DELIVERY DEVICE

CROSS-REFERENCE TO RELATED APPLICATIONS

This application is a continuation of U.S. patent application Ser. No. 17/174,011, filed Feb. 11, 2021, and entitled "Implant Delivery Device", which claims the benefit of Provisional Patent Application No. 62/972,775, filed on Feb. 11, 2020, and entitled "Graft Delivery Device," the entire disclosure of which is hereby incorporated by reference.

BACKGROUND

The present embodiments relate generally to medical devices, and in particular to medical devices used to repair tissue.

Rotator cuff repair is a surgical procedure performed to repair torn (or partially torn) tendons in the shoulder. This procedure can be done with large incisions or with arthroscopic techniques. To repair a torn tendon (such as the supraspinatus tendon), a surgeon may use anchors and sutures to reattach the tendon to the humerus bone. The repaired area may then be covered with a graft to facilitate healing. Inserting a graft through a small incision and laying it down in a desired position can be difficult with arthroscopic surgery.

There is a need in the art for a system and method that addresses the shortcomings discussed above.

SUMMARY

In one aspect, the present disclosure is directed to an implant delivery device including a handle disposed at a proximal end of the implant delivery device and configured to be grasped by a user. The device may further include an outer shaft extending from the handle to a distal end of the implant delivery device. In addition, the implant delivery device may include an implant holding portion proximate the distal end of the implant delivery device, the implant holding portion being configured to retain a sheet-like implant during implantation of the implant. Further, the implant holding portion may be configured to receive the implant between a fixed implant supporting flange member and configured to support the implant on one side, and a movable implant supporting flange member. The movable implant supporting flange member may be configured to be slidable between a first, distal position and a second, proximal position. In the first, distal position, the movable implant supporting flange member secures the implant against the fixed implant supporting flange member, thus holding the implant in an unfurled configuration. In the second, proximal position, the movable implant supporting flange member is withdrawn from the distal end of the implant delivery device, thus enabling release of the implant.

In another aspect, the present disclosure is directed to an implant delivery device including an implant holding portion proximate a distal end of the implant delivery device, the implant holding portion being configured to retain a sheet-like implant during implantation of the implant. The implant holding portion may be configured to receive the implant with a movable implant supporting flange member configured to retain the implant. The movable implant supporting flange member may be configured to be movable between a first position in which the movable implant supporting flange member holds the implant within the recess and a second position in which the implant is unencumbered by the movable implant supporting flange member, thus enabling release of the implant from the implant holding portion of the implant delivery device.

In another aspect, the present disclosure is directed to a method of delivering a sheet-like implant to a surgical site. The method may include providing an implant delivery device with a sheet-like implant secured by an implant holding portion of the implant delivery device such that the implant is held with respect to an outer shaft and between a fixed implant supporting flange member and a movable implant supporting flange member. The method may also include inserting the implant holding portion of the implant delivery device to a surgical site. Further, the method may include moving the movable implant supporting flange member to a second position, thereby allowing the implant to be released.

Other systems, methods, features, and advantages of the embodiments will be, or will become, apparent to one of ordinary skill in the art upon examination of the following figures and detailed description. It is intended that all such additional systems, methods, features, and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

FIG. 1 is a schematic view of a step in a procedure for repairing a rotator cuff tendon according to an embodiment;

FIG. 2 is a schematic view of a step of applying an implant to a portion of a rotator cuff tendon to facilitate healing according to an embodiment;

DETAILED DESCRIPTION

Figure 3:
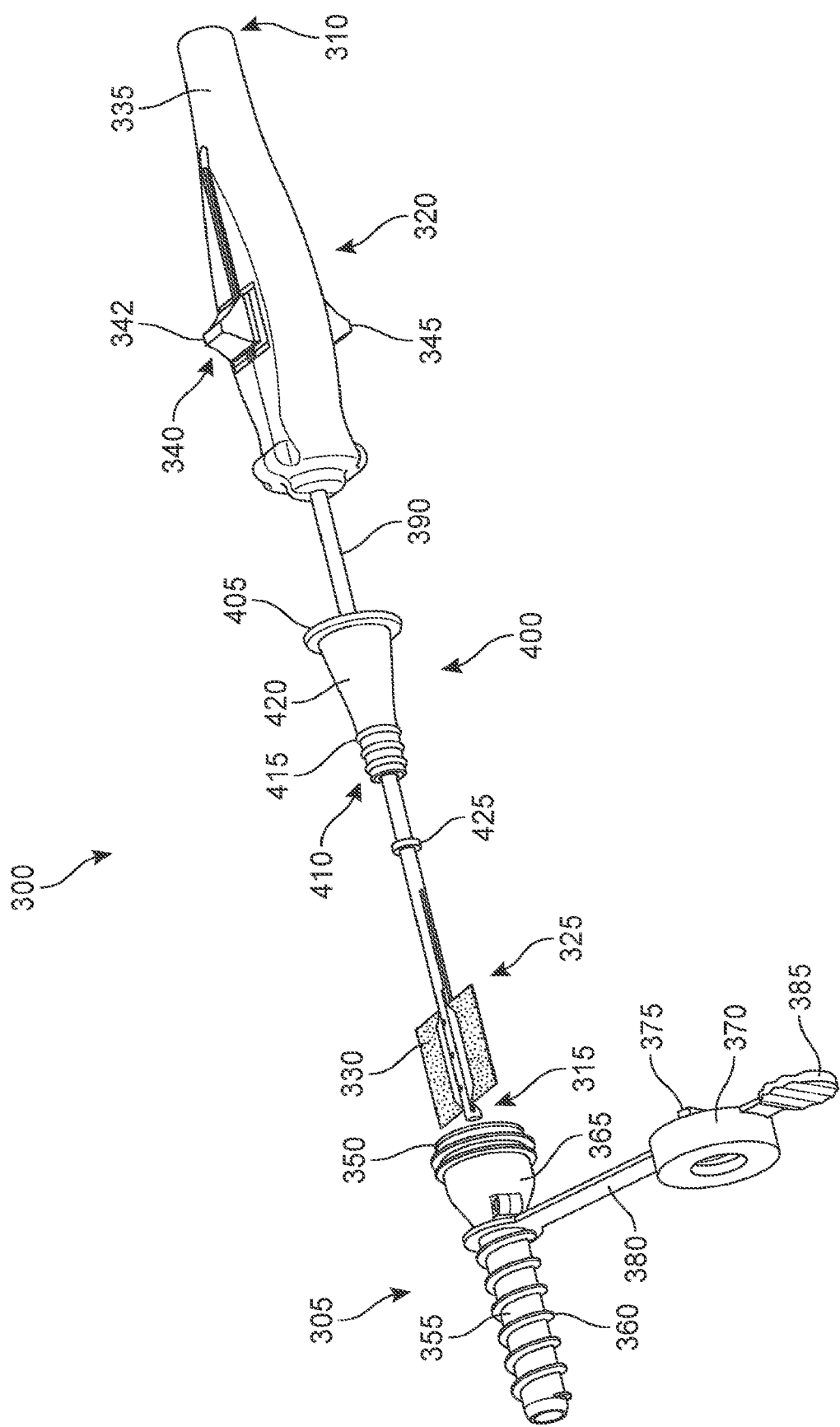
FIG. 3 is a schematic illustration of an implant delivery device according to an embodiment holding an implant prior to delivery through an illustrated access cannula.

For clarity, the description makes reference to distal and proximal directions (or portions). As used herein, the term "distal" shall refer to a direction or portion oriented or located away from a user who is holding the implant delivery device (i.e., away from a surgeon using the device and toward a patient into which the device is being inserted). The term "proximal" shall refer to a direction or portion oriented or located toward a user who is holding the implant delivery device (i.e., toward a surgeon using the device and away from a patient into which the device is being inserted).

In addition, as used herein, the term "fixedly attached" shall refer to two components joined in a manner such that the components may not be readily separated (for example, without destroying one or both components). The term "removably attached" shall refer to components that are attached to one another in a readily separable manner (for example, with fasteners, such as bolts, screws, etc.).

FIG. 1 is a schematic view illustrating a surgical procedure to repair a tendon in a patient's shoulder. Specifically, a patient 100 is undergoing arthroscopic surgery that is performed by surgeon 102. Also shown in FIG. 1 is an enlarged view of a portion of humerus 110 and rotator cuff tendons 112. In the present example, surgeon 102 has recently applied anchors and sutures to secure supraspinatus tendon 114 to humerus 110.

Once the tendon has been sufficiently repaired and/or the surgical site is otherwise prepared, surgeon 102 may insert an implant, such as a graft, through an incision (possibly using another device to facilitate insertion). The graft can then be placed over the tendon and/or portion of the underlying bone in order to facilitate healing. As an example, FIG. 2 shows a schematic view of a graft 202 that has been applied over the tendon 114 as well as over a portion of humerus 110.

Although the exemplary embodiment depicts a procedure in which a tendon is first secured to the bone using sutures and anchors, in other embodiments a graft can be applied to one or more tendons without first reattaching a tendon. For example, grafts could be applied to tendons that have only partial tears.

Once graft 202 has been placed over the tendon, one or more sutures or anchors are required to hold graft 202 in place. The present embodiments disclose a graft delivery device configured to hold an implant, such as a graft, during insertion and release the implant/graft once it has been secured at the surgical site.

An embodiment of an implant delivery device that can be used to insert an implant through a small incision and position it in over tissue in a fully opened condition is shown in FIGS. 3-19.

The implant delivery device may include provisions for biasing a sheet-like implant to an open, unfurled configuration as well as for releasing the implant once it has been placed in a desired location. The handle includes provisions to actuate components of an implant holding portion of the device. It will be understood that the disclosed implant delivery device may be configured to deliver any type of sheet-like implant. For example, in some embodiments, the delivery device may be used to deliver a sheet-like graft. In some embodiments, the graft may be formed, at least in part of collagen. In other embodiments, the sheet-like implant may be formed of synthetic material or blends of collagen and various synthetic polymers as are described, for example, in Francis et al., U.S. Pat. No. 10,617,787, issued Apr. 14, 2020, and entitled "Biopolymer Compositions, Scaffolds and Devices," the entire disclosure of which is incorporated herein by reference, and Francis et al., U.S. Pat. No. 10,653,817, issued May 19, 2020, and entitled "Method for Producing an Implantable Ligament and Tendon Repair Device," the entire disclosure of which is incorporated herein by reference.

The handle includes a slider member coupled to components that facilitate releasing the implant once it has been placed in a desired position in the body of the patient. The slider member and related components are described in further detail below and shown.

The deployment device may be designed to be easily held. To this end, the body may include a handgrip portion. The handgrip portion may be designed to accommodate either a left or right hand. A user's hand may engage the handgrip portion and use their fingers to actuate the slider member. Additionally, a user's finger(s) or thumb can be used to move the slider member. It may be appreciated that in some embodiments, a variety of different materials, coatings and/or surface treatments can be used with the handle and/or the slider member to improve grip and prevent slipping.

In some embodiments, the disclosed implant delivery device may be configured for insertion through a medical cannula. Medical cannulas are generally well-known in the art of arthroscopic surgery. For example, various types of cannulas are used to control the inflow or outflow of fluids, to allow access for tools into the tissue, and for other functions. In some types of surgeries, an implant or other substrate material may be introduced into a surgical site through a cannula, which maintains an enlarged access port to the surgical site. Additionally, many arthroscopic surgeries, such as joint surgeries, use pressurized irrigation fluid to keep tissue separated apart from other tissue. In particular, pressurized irrigation fluid may be used to aid in visualization of the surgical site as well as to prevent bleeding from vasculature surrounding the surgical cuts. Other types of surgeries, such as gastrointestinal procedures, use pressurized gas to provide access to and visualization of the surgical site.

Utilizing a cannula eliminates the need to include an outer sheath covering the implant during insertion. That is, if the implant is inserted through an incision in the bare skin of the patient, the implant, which is typically relatively delicate, is typically preferred to be encased. Accordingly, implant delivery devices configured to introduce implants directly through the skin (i.e., without a cannula) typically include a sheath that covers the implant during insertion and which is then retracted to expose the implant once the distal end of the instrument reaches the surgical site. Alternatively, devices may include a fixed outer sheath and a movable inner component that holds the implant within the sheath during insertion and is then moved distally to expose the implant at the surgical site.

The presently disclosed implant delivery device is devoid of implant-covering sheathes. Instead, the disclosed device includes resilient implant supporting flange members that pinch the implant generally along a midline of the implant. The flange members abut against a partial area of both sides of the implant. The resilient flange members thus bias the implant toward an unfurled configuration. However, because both the implant and flange members are flexible, the implant (and flange members) may roll up when delivered through a surgical cannula. When the distal end of the device exits the distal end of the cannula, the flange members bias the implant into an unfurled condition. The implant can then be positioned over the tendon and/or bone at the surgical site. In addition, the implant delivery device can be used to hold the implant in place while anchors are used to secure the implant to the native tissue/bone.

FIG. 3 is a schematic illustration of an implant delivery device according to an embodiment holding an implant prior to delivery through an illustrated access cannula. As shown in FIG. 3, an implant delivery device 300 may be configured to be inserted through a cannula 305. As further shown in FIG. 3, implant delivery device 300 may have a proximal end 310 and a distal end 315. In addition, implant delivery device 300 may include a handle 320 disposed at proximal end 310 of implant delivery device 300 and configured to be grasped by a user.

Implant delivery device 300 may include an implant holding portion 325 proximate distal end 315 of implant delivery device 300, implant holding portion 325 being configured to retain a sheet-like implant 330 during implantation of implant 330.

Handle 320 may include a casing 335 including a slider member 340 configured to actuate an implant release mechanism discussed in greater detail below. In some embodiments, handle 320 may include an ambidextrous configuration. For example, as shown in FIG. 3, slider member 340 may include a first slider 342 and a second slider 345. As shown in later FIGS. (see, e.g., FIG. 18), first slider 342 may be attached to or integral with second slider 345. Thus, actuating either slider will have the same effect. Accordingly, a surgeon can use either hand and hold the device in a variety of orientations and still have ready access to slider member 340.

Casing 335 of handle 320 may be formed of a substantially rigid material, such as a hard/rigid plastic and/or metal. Casing 335 must substantially maintain its shape and structural integrity during manipulation of implant delivery device 300 as handle 320 is the portion of the device to which forces are applied during use. Further, the connection between handle 320 and outer shaft 390 must be configured to withstand this loading.

As shown in FIG. 3, exemplary cannula 305 may have a proximal end 350 with a wider mouth opening and a narrower distal portion 355 including threads 360. Cannula 305 may include a tapered intermediate portion 365 between proximal end 350 and distal portion 355. Implant delivery device 300 may be configured such that, when passing implant 330 through cannula 305, tapered intermediate portion 365 may roll up implant 330. As further shown in FIG. 3, cannula 305 may include a seal structure 370. Seal structure may include a seal 375. Seal 375 may be any type of seal suitable for passing instruments, such as obturators through. For example, as shown in the accompanying figures, seal 375 may be a duckbill valve. In other embodiments, seal 375 may be a tricuspid valve. In some embodiments, seal structure 370 may include more than one seal in series. In addition, seal structure 370 may include a tether 380 for connecting seal structure 370 to cannula 305. Further, seal structure 370 may include a grasping tab 385. It will be understood that cannula 305 and seal structure 370 may have any suitable configurations for passing implants therethrough using implant delivery device 300. Implant delivery device 300 may be configured for use with cannulas having any of the features disclosed in Jones et al., U.S. patent application Ser. No. 17/173,531, filed Feb. 11, 2021, and entitled "Surgical Cannula with Removable Pressure Seal," the entire disclosure of which is incorporated herein by reference.

Further, implant delivery device 300 may include an outer shaft 390 extending from handle 320 to distal end 315 of implant delivery device 300. Outer shaft 390 may be formed out of a substantially rigid material that is also biocompatible. For example, outer shaft 390 may be formed out of surgical stainless steel or titanium. In some embodiments, outer shaft 390 may be formed to have substantially no deflection when subjected to the forces of implant delivery. In other embodiments, outer shaft 390 may be configured to have a predetermined amount of flexibility in order to facilitate placement of the implant via manipulation of the handle. It will be understood that, also contemplated are configurations where the implant is not necessarily attached to a shaft, but attached to an alternative structure at the distal end of the device.

In addition, as shown in FIG. 3, implant delivery device 300 may further include a cannula sealing member 400 disposed about a midportion of outer shaft 390. Cannula sealing member 400 may include a proximal flange 405 for abutting proximal end 350 of cannula 305. In addition, cannula sealing member 400 may include a narrower distal portion 410 configured to fit within narrow distal portion 355 of cannula 305. Distal portion 410 of cannula sealing member 400 may include one or more ribs 415 configured to seal against the inner wall of distal portion 355 of cannula 305. In addition, cannula sealing member 400 may include a tapered intermediate portion 420 between proximal flange 405 and narrow distal portion 410.

When implant insertion device 300 is to be inserted through cannula 305, seal structure 370 may be removed from proximal end 350 of cannula 305. In order to maintain pressure at the surgical site, cannula sealing member 400 may be inserted into cannula 305 as implant delivery device 300 is passed through cannula 305. Cannula sealing member 400 may be slidable along outer shaft 390 of implant insertion device 300 in order to facilitate manipulation of implant insertion device 300 to and about the surgical site.

As also shown in FIG. 3, outer shaft 390 of implant delivery device 300 may include a ring 425 disposed distal to cannula sealing member 400 and configured to pull cannula sealing member 400 out of cannula 305 when handle 320 of implant delivery device 300 is pulled in the proximal direction to withdraw implant delivery device 300 from the surgical site.

Figure 4:
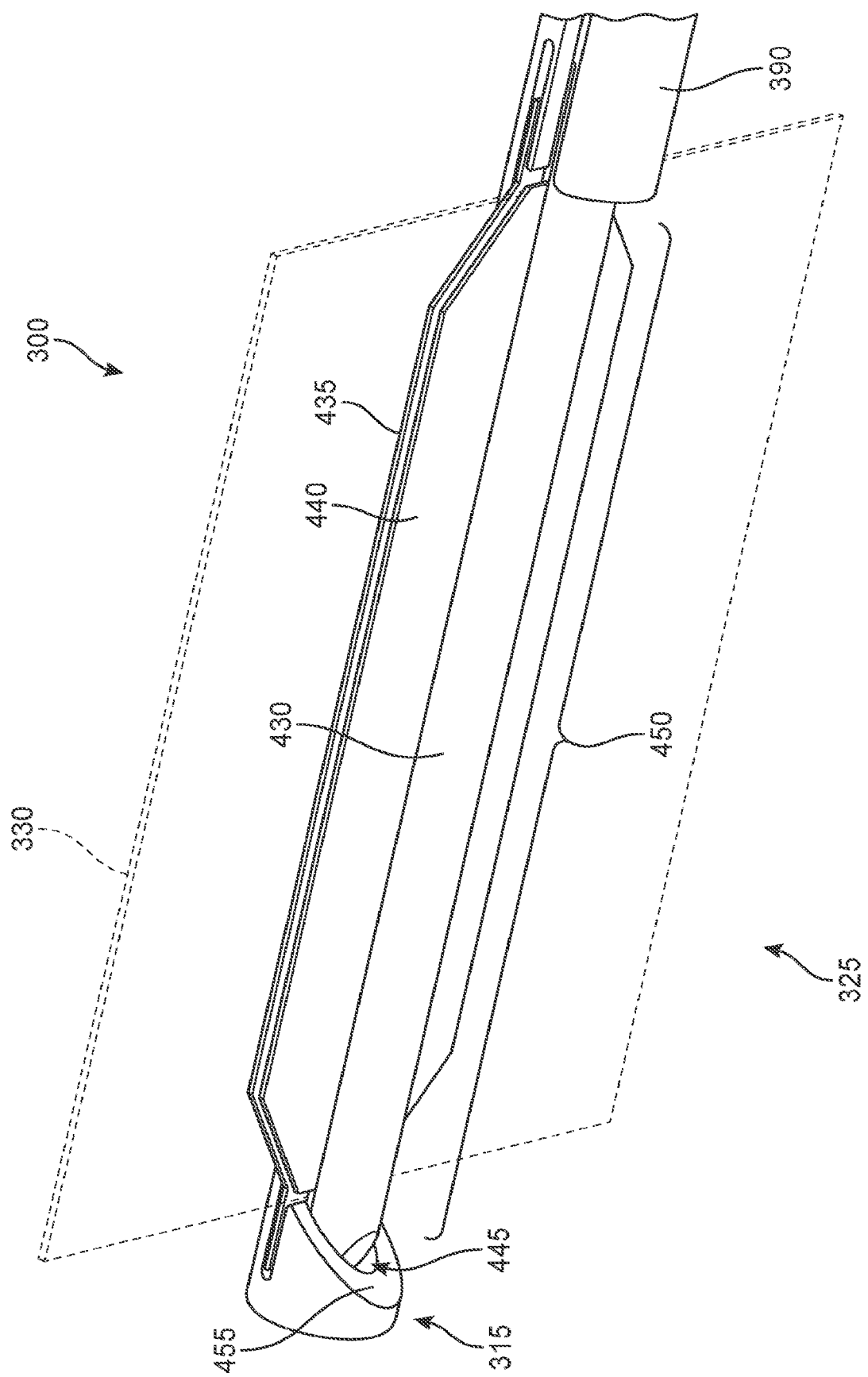
FIG. 4 is an enlarged schematic view of an implant holding portion of the implant delivery device holding an implant.

FIG. 4 is an enlarged schematic view of an implant holding portion of the implant delivery device holding an implant. In particular, as shown in FIG. 4, implant holding portion 325 may include a recess 450 configured to receive implant 330, a fixed implant supporting flange member 435 disposed within recess 450 and configured to support implant 330 on one side, and a movable implant supporting flange member 440. Fixed implant supporting flange member 435 may be fixedly attached to outer shaft 390 within recess 450. Movable implant supporting flange member 440 may be configured to be slidable between a first, distal position and a second, proximal position. In the first, distal position, movable implant supporting flange member 440 is disposed within recess 450 and secures implant 330 against fixed implant supporting flange member 435, thus holding implant 330 in recess 450 in an unfurled configuration, as shown in FIG. 4. It will be noted that, although the flange members are not as large as the implant, the partial support provided by the smaller flange members is enough to maintain the implant in a substantially unfurled condition. Depending on the type of implant with which the device is to be used, and the relative stiffness of the implant, the flange members may vary in stiffness and/or size. In addition, the distance between the flange members may vary depending on the thickness of the implant and the relative compressibility of the implant in order to ensure suitable clamping force between the flange members.

Fixed implant supporting flange member 435 and movable implant supporting flange member 440 may be formed of a flexible but resilient material. That is, the material may be able to flex relatively easily, but return to the flat configuration when the loading is removed.

In addition, since fixed implant supporting flange member 435 and movable implant supporting flange member 440 are exposed to the surgical site, they may be formed of a biocompatible material. Such biocompatible plastics may include the following: polyethylene, polypropylene, polyimide (Kapton®), acrylonitrile butadiene styrene and PAEK polymers. In some embodiments, implant supporting flange members formed of such materials may have thicknesses of approximately 0.001 to 0.025 inch. Other possible materials for the flange members may include nitinol, stainless steel, and/or titanium. Implant supporting flange members formed of such metallic materials may be formed in the appropriate thickness to match the properties of flange members formed of the non-metal materials mentioned above.

As also shown in FIG. 4, movable implant supporting flange member 440 may be attached to an inner shaft 430, which may be translated in the proximal and distal directions to slide movable implant supporting flange member 440. Further, distal end 315 of implant delivery device 300 may include a recess 445 at the end of outer shaft 390 for receiving a distal tip of inner shaft 430. Since at least a portion of inner shaft 430 is exposed to the surgical site, inner shaft 430 may also be formed of a biocompatible material, such as surgical stainless steel or titanium.

In addition, as also shown in FIG. 4, a distal wall 455 of recess 450 may be beveled. This bevel may facilitate release of implant 330, and removal of implant delivery device 300 from the surgical site as it is withdrawn across a delivered implant. That is, when removing implant delivery device 300, the bevel of distal wall 455 may enable outer shaft 390 to slide past implant 330 without catching on an edge of implant 330.

Figure 5:
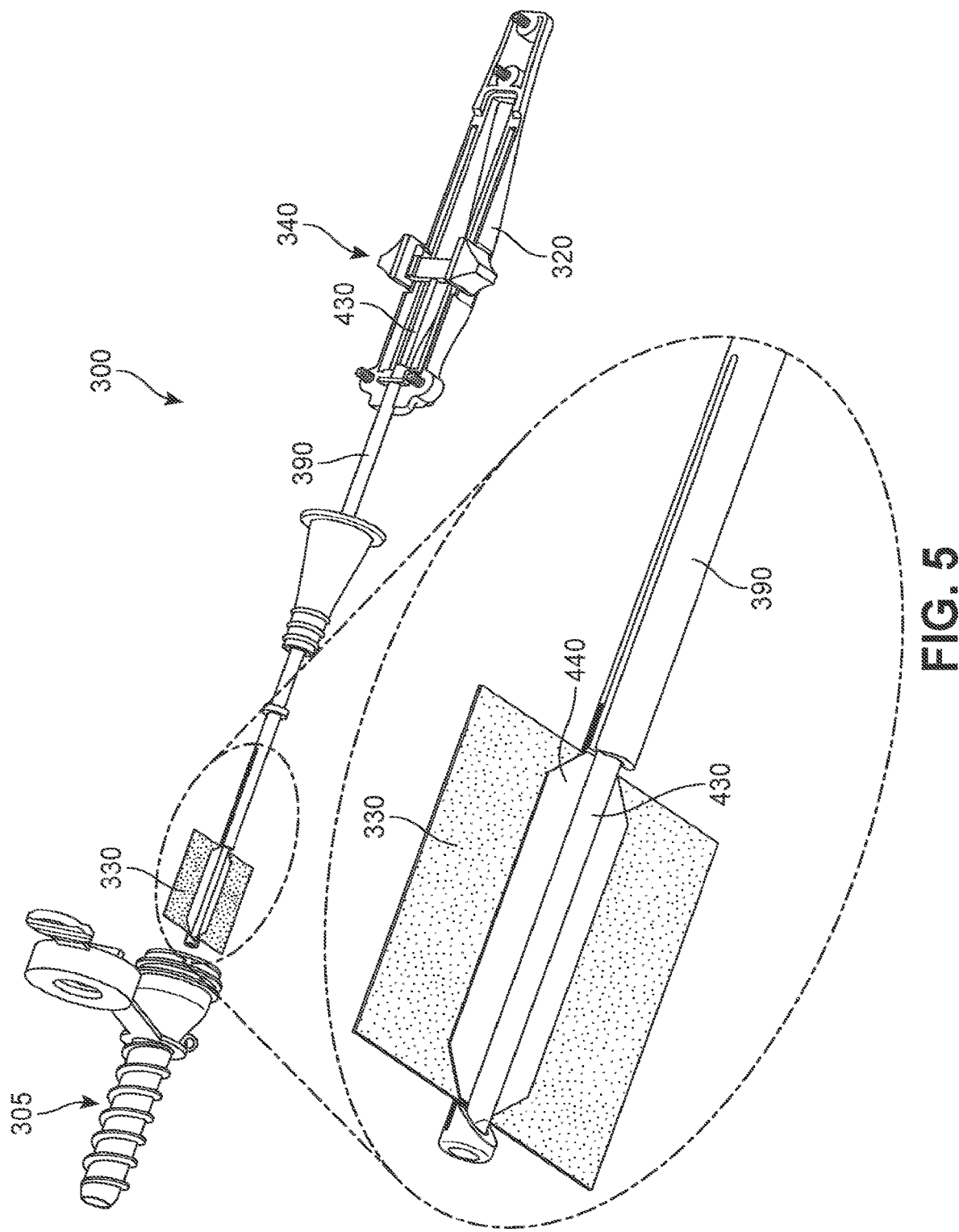
FIG. 5 is another schematic view of an implant delivery device according to an embodiment holding an implant prior to delivery through an illustrated access cannula.

FIG. 5 is another schematic view of implant delivery device 300 holding implant 300 prior to delivery through cannula 305. Panel 335 (FIG. 3) is removed in FIG. 5 in order to expose the inner mechanics of handle 320. Slider member 340 may be configured to be moved in the proximal and distal directions in order to slide movable implant supporting flange member 440 between the first, distal position discussed above and shown in FIG. 5 (as well as FIGS. 3 and 4) and a second, proximal position (shown in FIG. 16 and discussed in further detail below) wherein movable implant supporting flange member 440 is withdrawn from the recess in outer shaft 390 (see recess 445, shown in FIG. 4), thus enabling release of implant 330 from the recess.

It will be understood that, in some embodiments, the sliding movement of the movable implant supporting flange member may be opposite. That is, the movable flange member may be slid in the distal direction to release the implant. In still other embodiments, the movable implant supporting flange member may be moved in an alternative non-sliding manner to release the implant. For example, in some embodiments, the movable implant supporting flange member may be moved with respect to the fixed implant supporting flange member in a clamshell type action. In some cases, the clamshell opening may occur at the proximal end or distal end of the implant. In other cases, the clamshell opening may be at one lateral side of the implant or the other.

FIG. 5 also includes an enlarged view of the implant holding portion of implant delivery device 300. In this view, FIG. 5 shows movable implant supporting flange member 440 disposed against implant 330, preventing implant 330 from being released. FIG. 5 also shows inner shaft 430 extending through outer shaft 390 and connecting slider member 340 in handle 320 to movable implant supporting flange member 440 at the distal end of implant delivery device 300.

Figure 6:
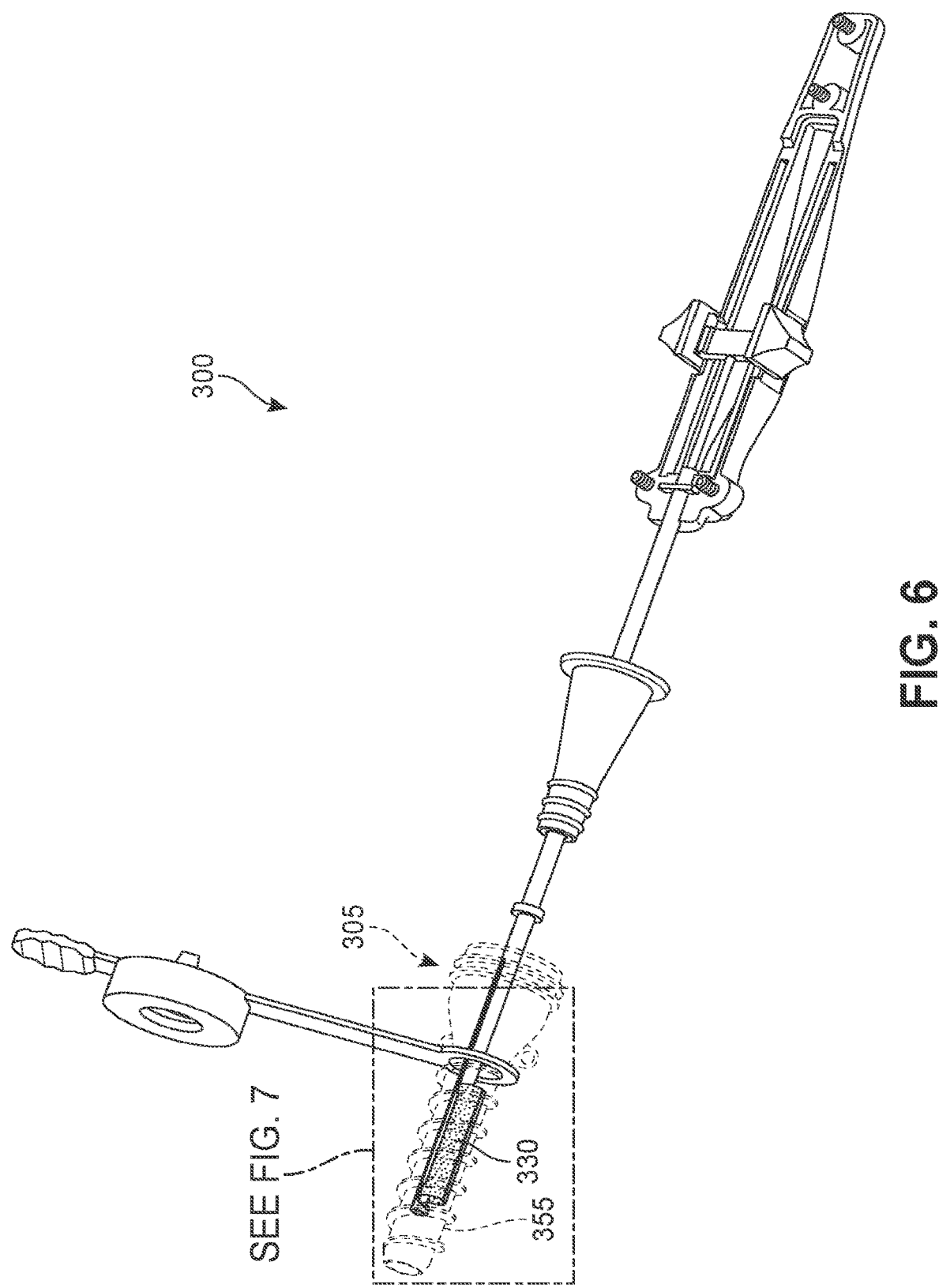
FIGS. 6-7 are schematic views showing the implant being inserted through the cannula.
Figure 7:
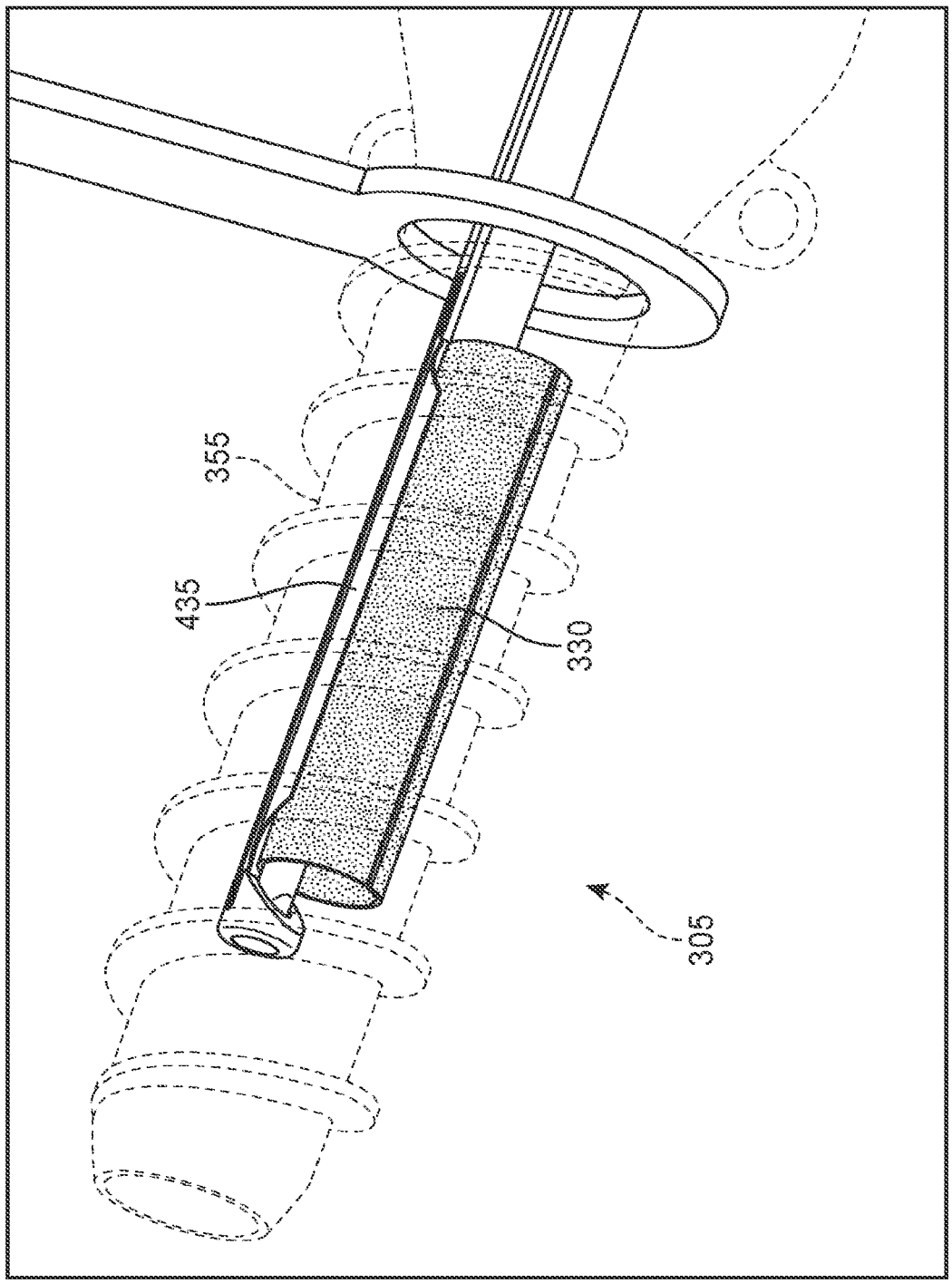

FIGS. 6-7 are schematic views showing the implant being inserted through the cannula. FIG. 6 shows cannula 305 in phantom in order to reveal the implant holding portion of implant delivery device 300 along with implant 330 being passed through cannula 305. As shown in FIG. 6, and more clearly shown in FIG. 7, implant 330 may roll up when being passed through cannula 305.

It will be understood that the fixed implant supporting flange member (435; FIG. 4) and the movable implant supporting flange member (440; FIG. 4) are flexible and resilient such that the fixed implant supporting flange member and the movable implant supporting flange member may be collapsed/deflected upon delivery through cannula 305. In some cases, as shown in FIG. 7, the flange members and implant 330 may roll up in order to facilitate passage of implant 330 through cannula 305 and to provide protection for implant 330 during this passage. It will be understood, however, that the implant and the flange members may fold, wrinkle, or otherwise collapse in a uniform or non-uniform manner upon insertion through the cannula. In other words, the implant and the flange members may have a constrained condition or form in which these elements are at least partially collapsed, and an unconstrained condition or form in which these elements are substantially unfurled. The collapsed/constrained condition may occur in situ, as the surgeon passes the distal end of the delivery device with the implant through a cannula. This collapsed/constrained condition may be a "non-use" condition of the implant, whereas the (substantially) unfurled condition may be a "use" condition.

Figure 8:
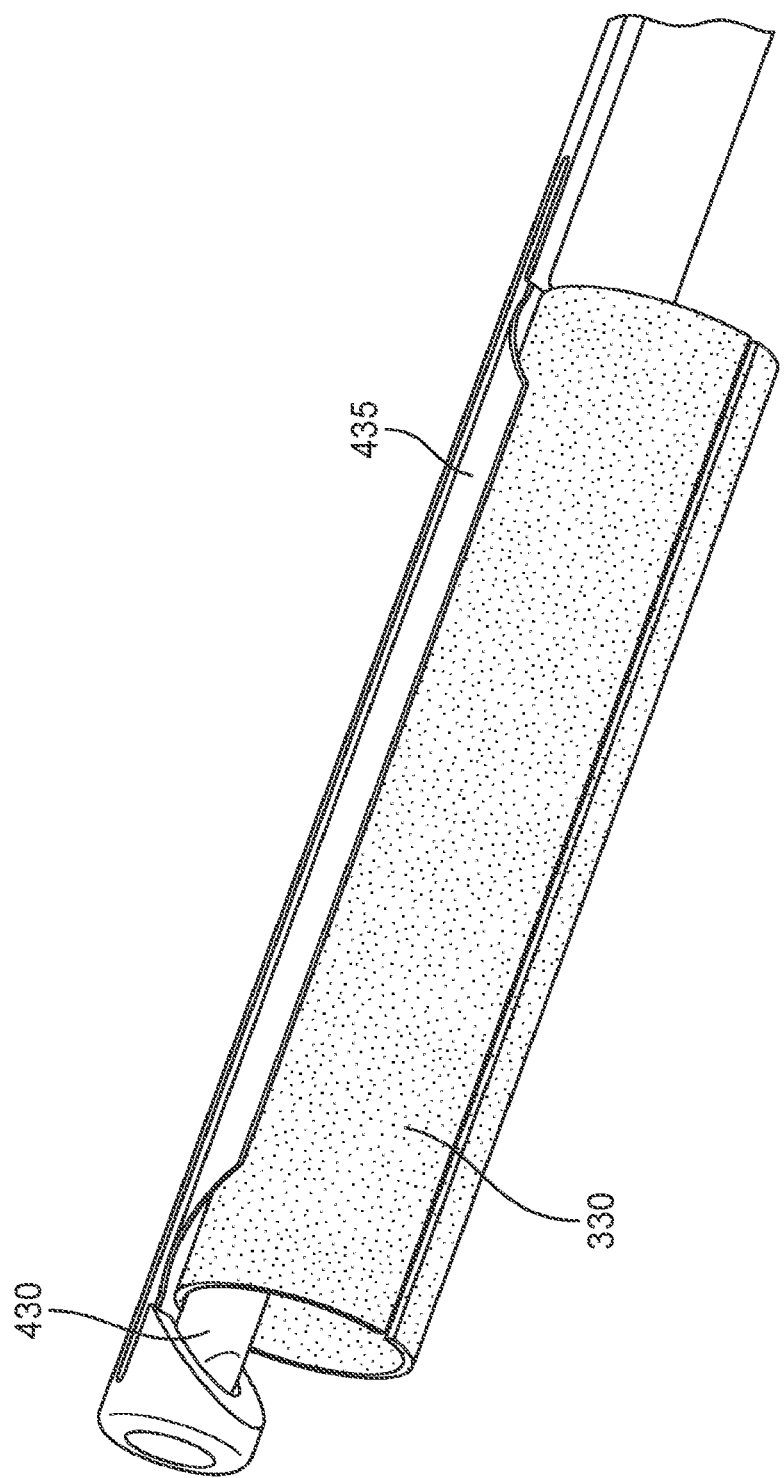
FIG. 8 is a schematic view of the implant being rolled up as it is during delivery through the cannula, but with the cannula removed for purposes of illustration.

FIG. 8 is a schematic view of the implant being rolled up as it is during delivery through the cannula, but with the cannula removed for purposes of illustration. As shown in FIG. 8, not only is implant 330 collapsed, but fixed implant supporting flange member 435 is also collapsed along with implant 330. Although inside the collapsed implant 330, movable implant supporting flange member (440) is also collapsed.

Figure 9:
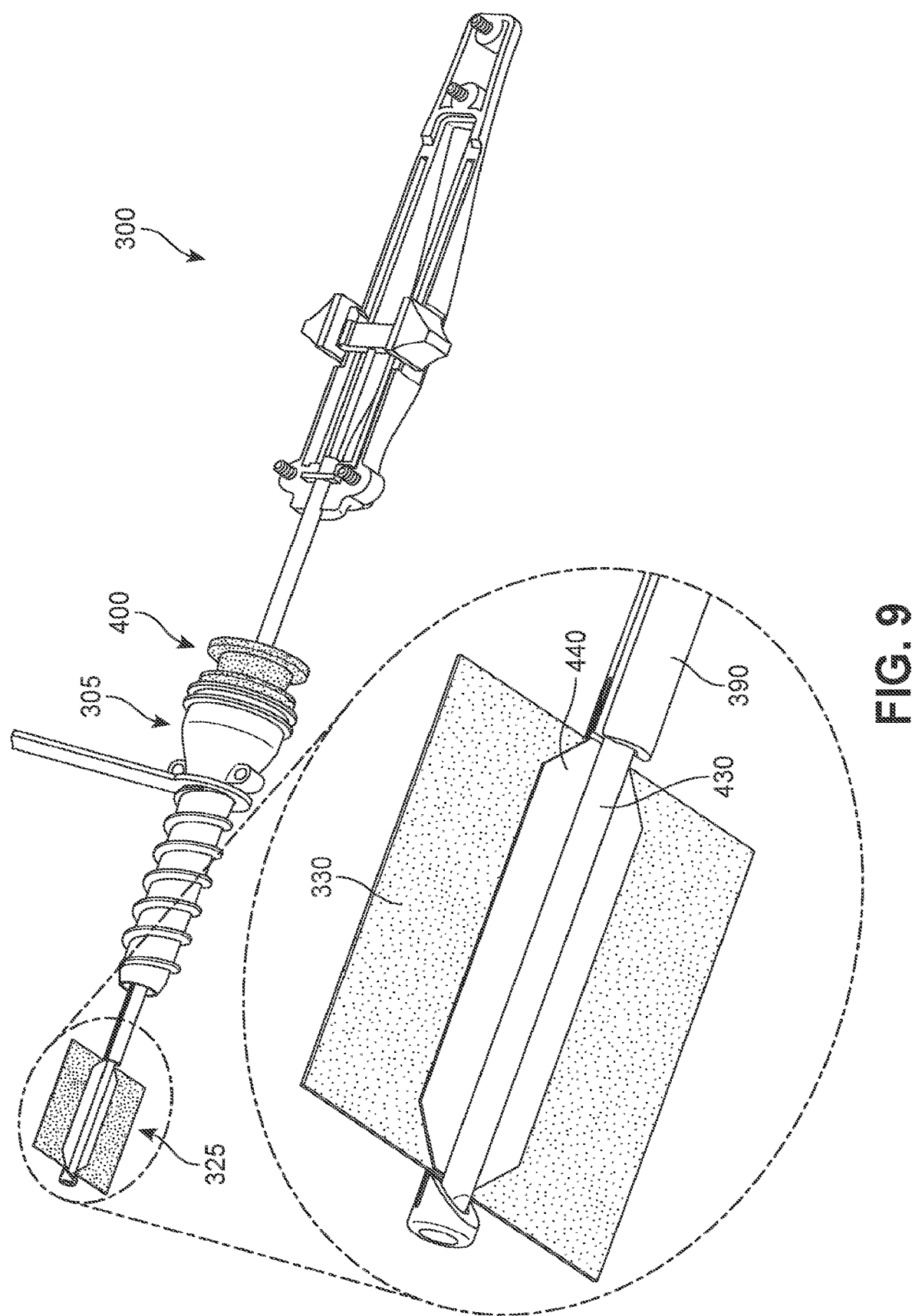
FIG. 9 is a schematic view of the implant delivery device extending through the cannula with the cannula sealing member seated within the cannula and with the implant unfurled after exiting the cannula.

FIG. 9 is a schematic view of the implant delivery device extending through the cannula with the cannula sealing member seated within the cannula and with the implant unfurled after exiting the cannula. In particular, FIG. 9 shows implant holding portion 325 of implant delivery device 300 extending beyond the distal end of cannula 305. Accordingly, implant 330 is unfurled in this position, since the cannula is no longer surrounding implant 330 to keep it rolled up.

FIG. 9 also shows cannula sealing member 400 seated within cannula 305. In this configuration of the components, pressure may be maintained within the surgical site and the implant is ready to be anchored to the tissue/bone and then released from implant holding portion 325 of implant delivery device 300.

Figure 10:
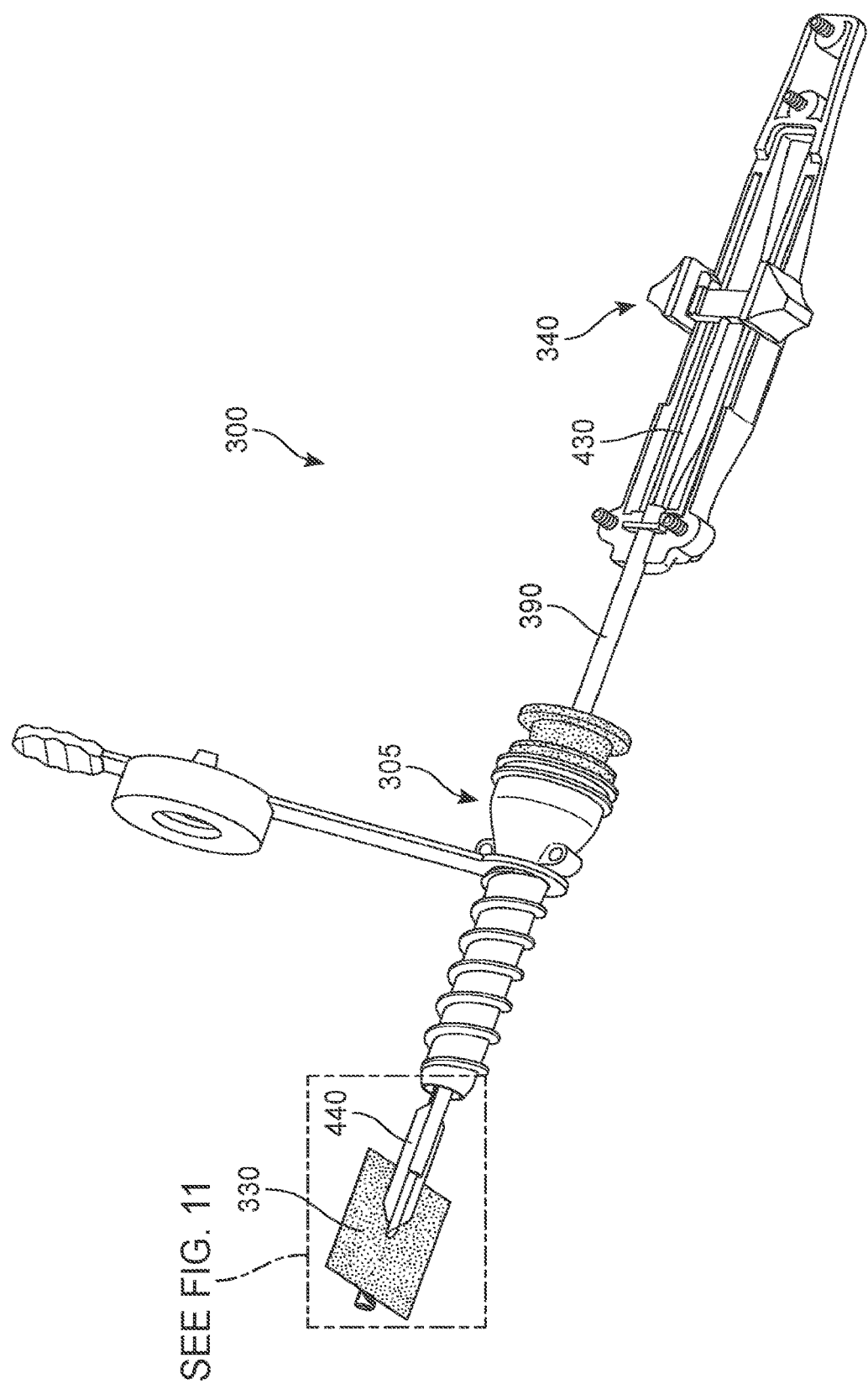
FIG. 10 is a schematic view of the implant delivery device with an implant supporting flange member partially withdrawn part way through the process of releasing the implant.

FIG. 10 is a schematic view of the implant delivery device with an implant supporting flange member partially withdrawn part way through the process of releasing the implant. As shown in FIG. 10, slider 340 has been moved proximally a portion of its permitted travel. Accordingly, inner shaft 430 has moved proximately, thus sliding the attached movable implant supporting flange member 440 in the proximal direction. It will be noted that there are not necessarily any detents that stop the mechanism at this stage of withdrawal. This is an intermediate condition illustrated simply to facilitate demonstration of the process of withdrawing movable implant supporting flange member 440.

Figure 11:
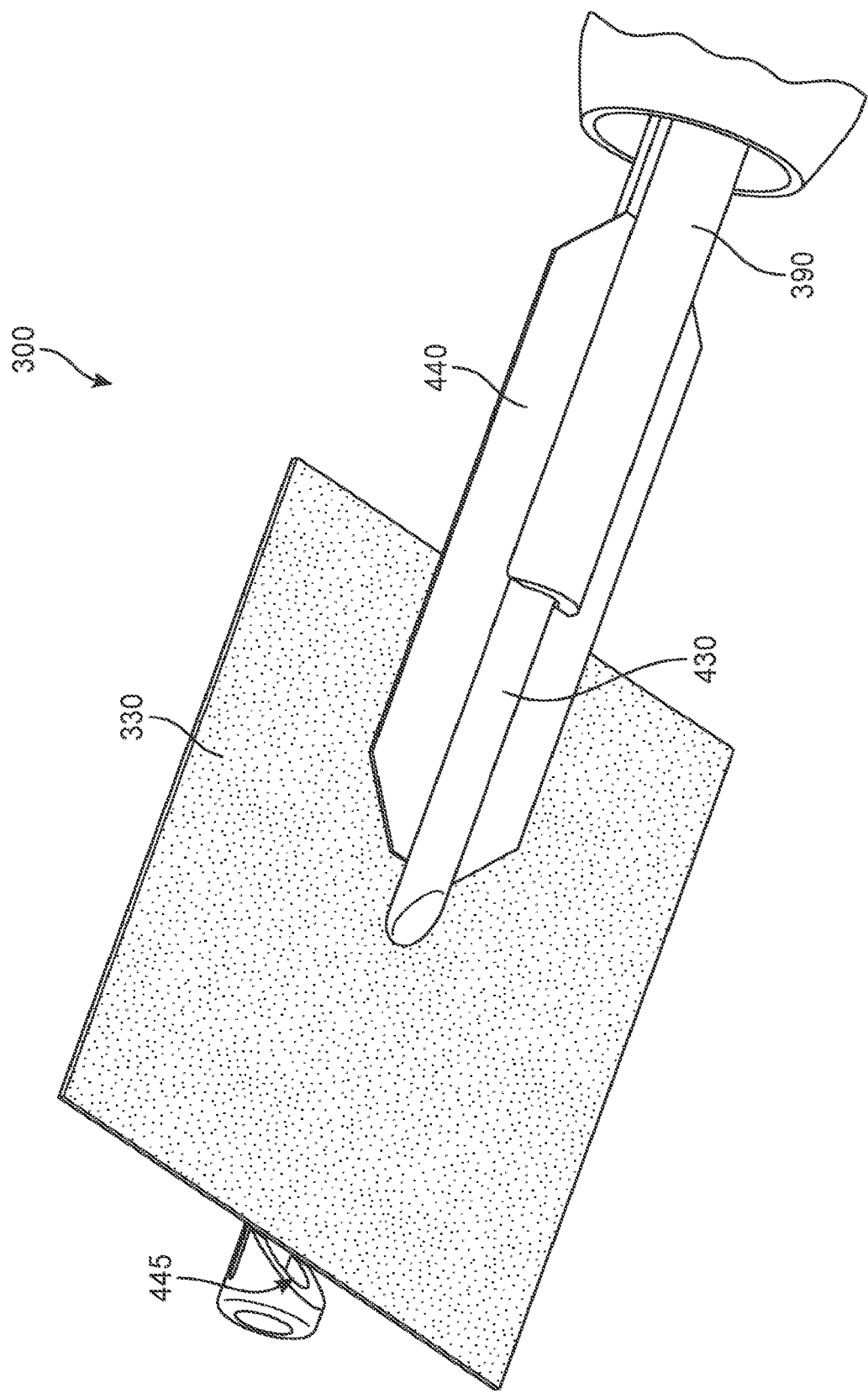
FIG. 11 is an enlarged schematic view of the implant holding portion of the implant delivery device with the implant supporting flange member partially withdrawn, as shown in FIG. 10.

FIG. 11 is an enlarged schematic view of the implant holding portion of the implant delivery device with the implant supporting flange member partially withdrawn, as shown in FIG. 10. As illustrated in FIG. 11, inner shaft 430 is partially withdrawn, as is movable implant supporting flange member 440 attached thereto. In this condition, the distal half of implant 330 is no longer supported on both sides. Again, this intermediate condition is merely shown for purposes of illustrating the translation of movable implant supporting flange member 440.

Figure 12:
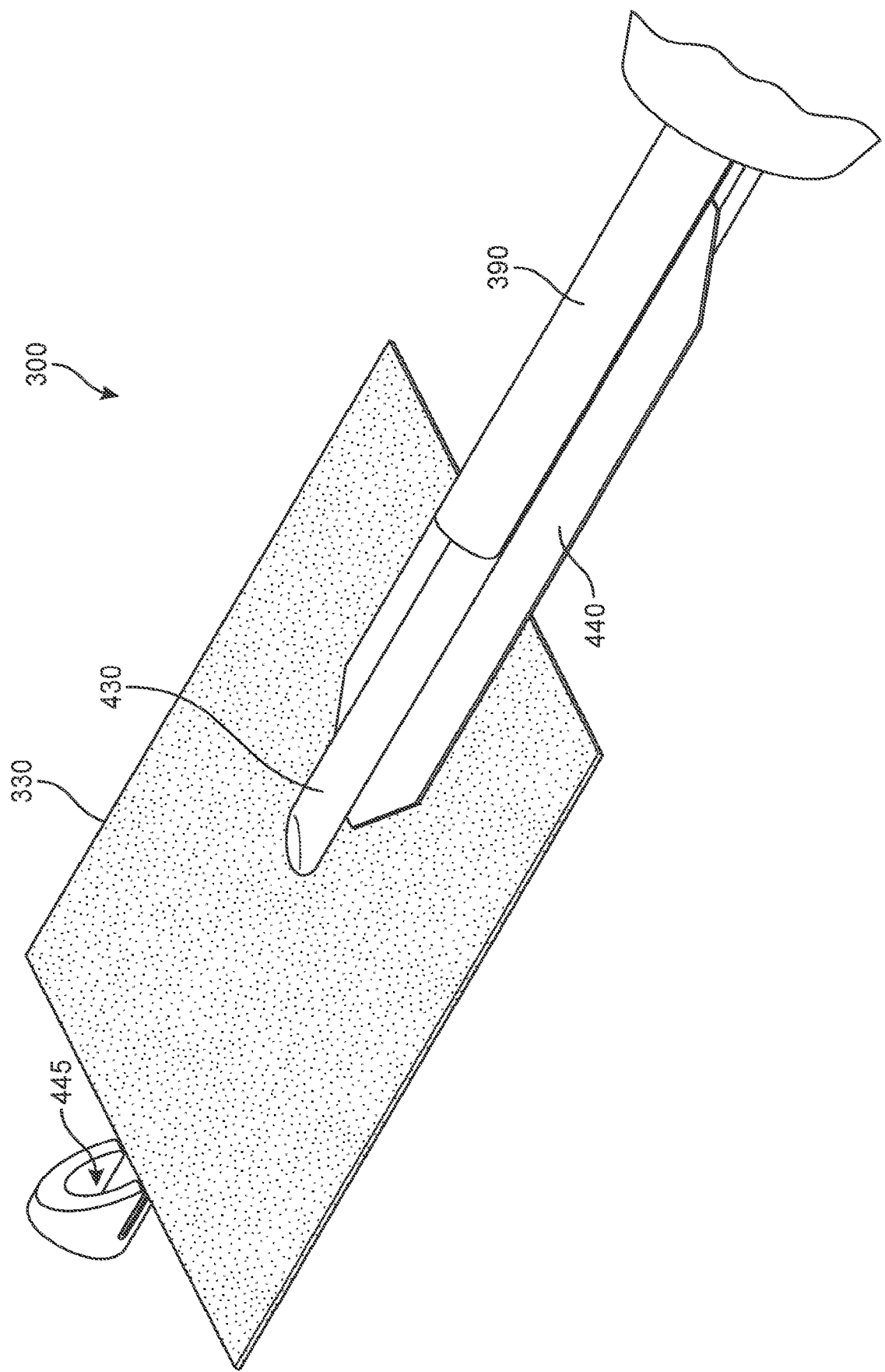
FIG. 12 is another enlarged schematic view of the implant holding portion of the implant delivery device with the implant supporting flange member partially withdrawn.

FIG. 12 is another enlarged schematic view of the implant holding portion of the implant delivery device with the implant supporting flange member partially withdrawn. FIG. 12 shows recess 445 into which the distal end of inner shaft 430 is disposed when movable implant supporting flange member 440 is in the distal (i.e., implant holding) position.

Figure 13:
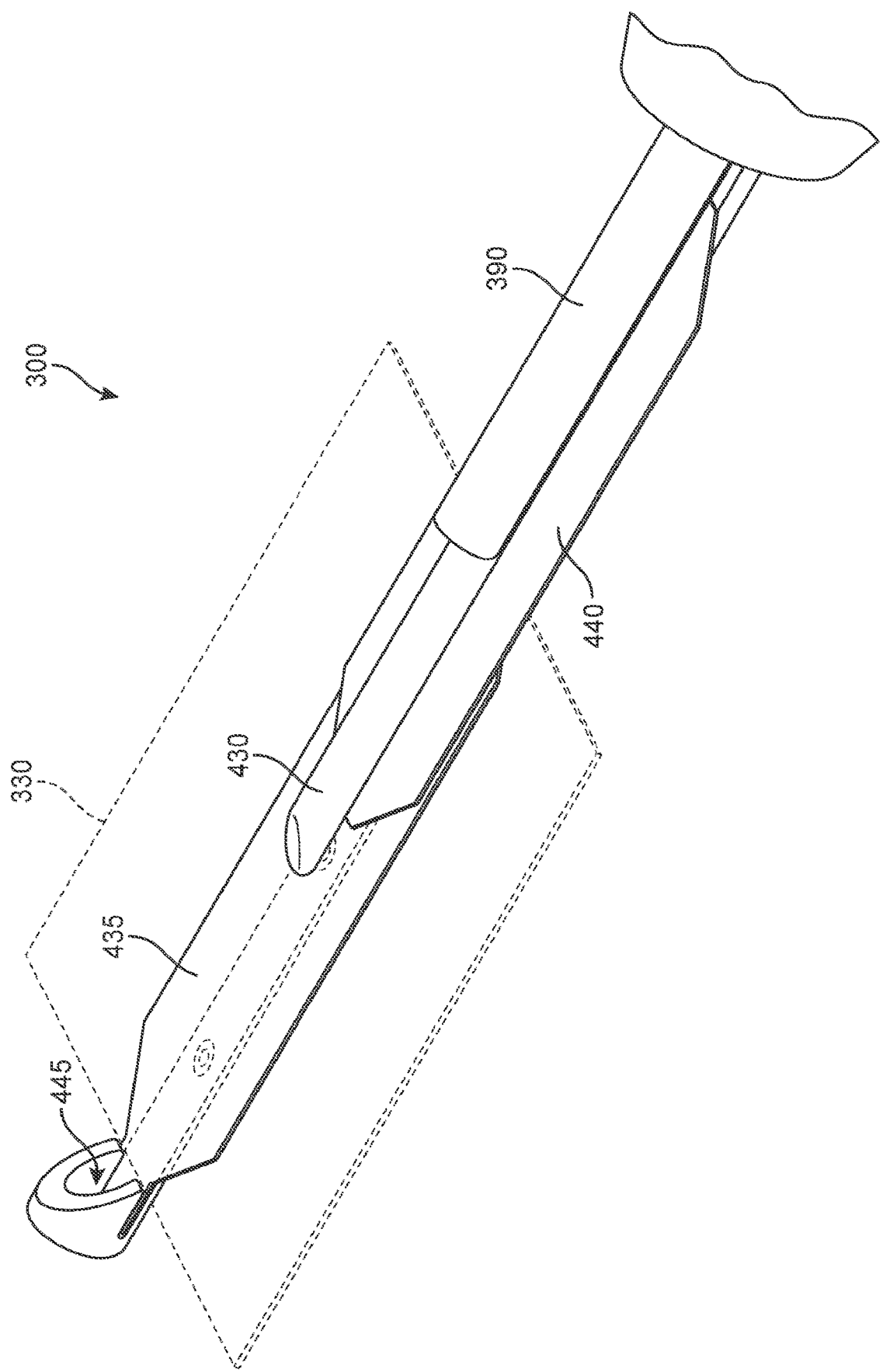
FIG. 13 is another enlarged schematic view of the implant holding portion of the implant delivery device with the implant supporting flange member partially withdrawn and with the implant shown in phantom in order to illustrate a second implant supporting member under the implant.

FIG. 13 is another enlarged schematic view of the implant holding portion of the implant delivery device with movable implant supporting flange member 440 partially withdrawn and with implant 330 shown in phantom in order to illustrate fixed implant supporting member 435 under implant 330. FIG. 13 illustrates how fixed implant supporting flange member 435 remains in place, fixed to outer shaft 390 and movable implant supporting flange member 440 has been moved proximally relative to fixed implant supporting flange member 435.

Figure 14:
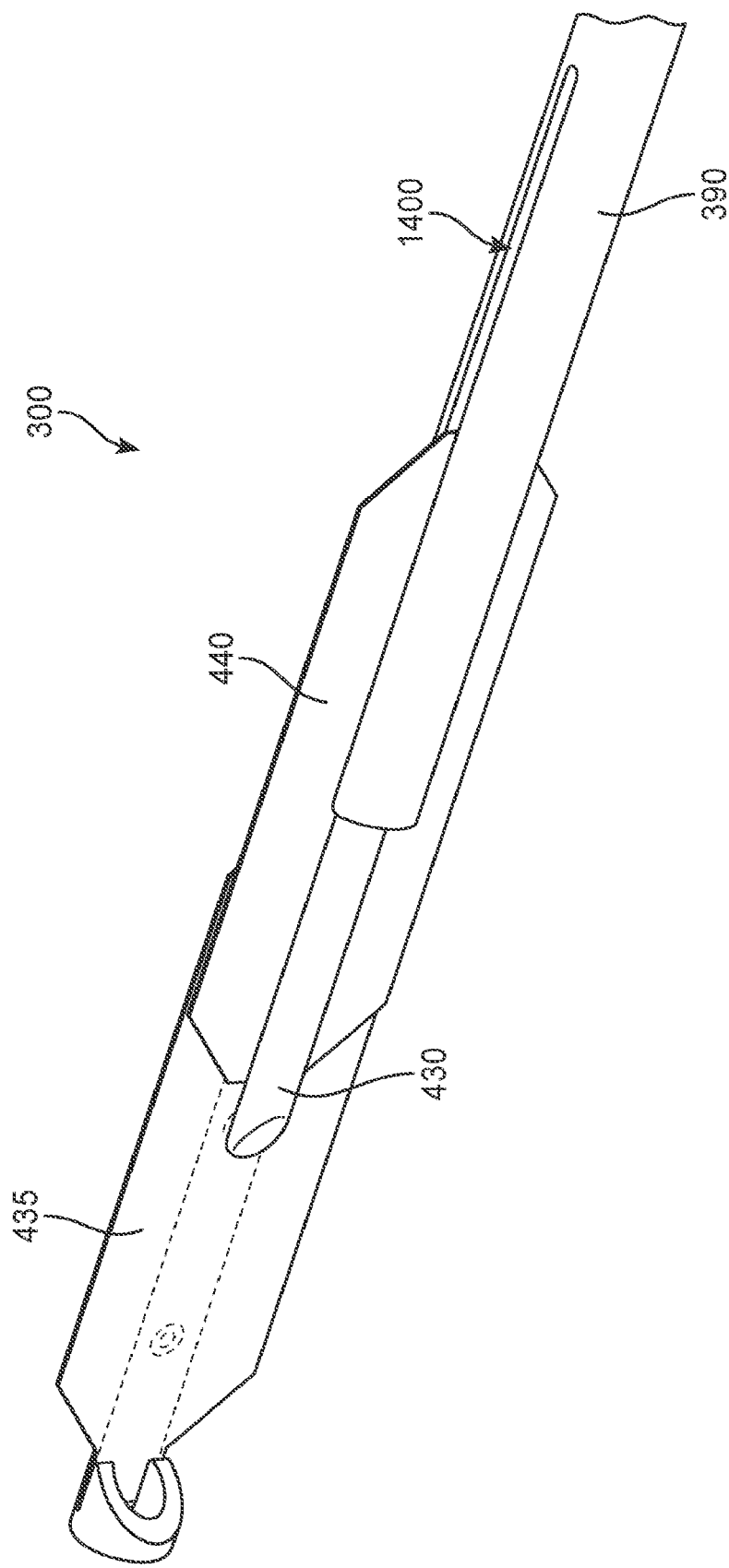
FIG. 14 is an enlarged schematic view of the implant holding portion of the implant delivery device with the implant supporting flange member partially withdrawn and with the implant omitted in order to illustrate the relationship between the two implant supporting flange members.

FIG. 14 is an enlarged schematic view of the implant holding portion of the implant delivery device with the implant supporting flange member partially withdrawn and with the implant omitted in order to illustrate the relationship between the two implant supporting flange members. Again, fixed implant supporting flange member 435 remains in place at the distal end of implant delivery device 300 and movable implant supporting member 440 has been moved proximally relative to fixed implant supporting flange member 435 and outer shaft 390. In order to facilitate this movement of movable implant supporting flange member 440, outer shaft 390 may include a slot 1400. As shown in FIG. 14, outer shaft 390 may include slot 1400 into which movable implant supporting flange member 440 is slid when inner shaft 430 is moved in the proximal direction.

Figure 15:
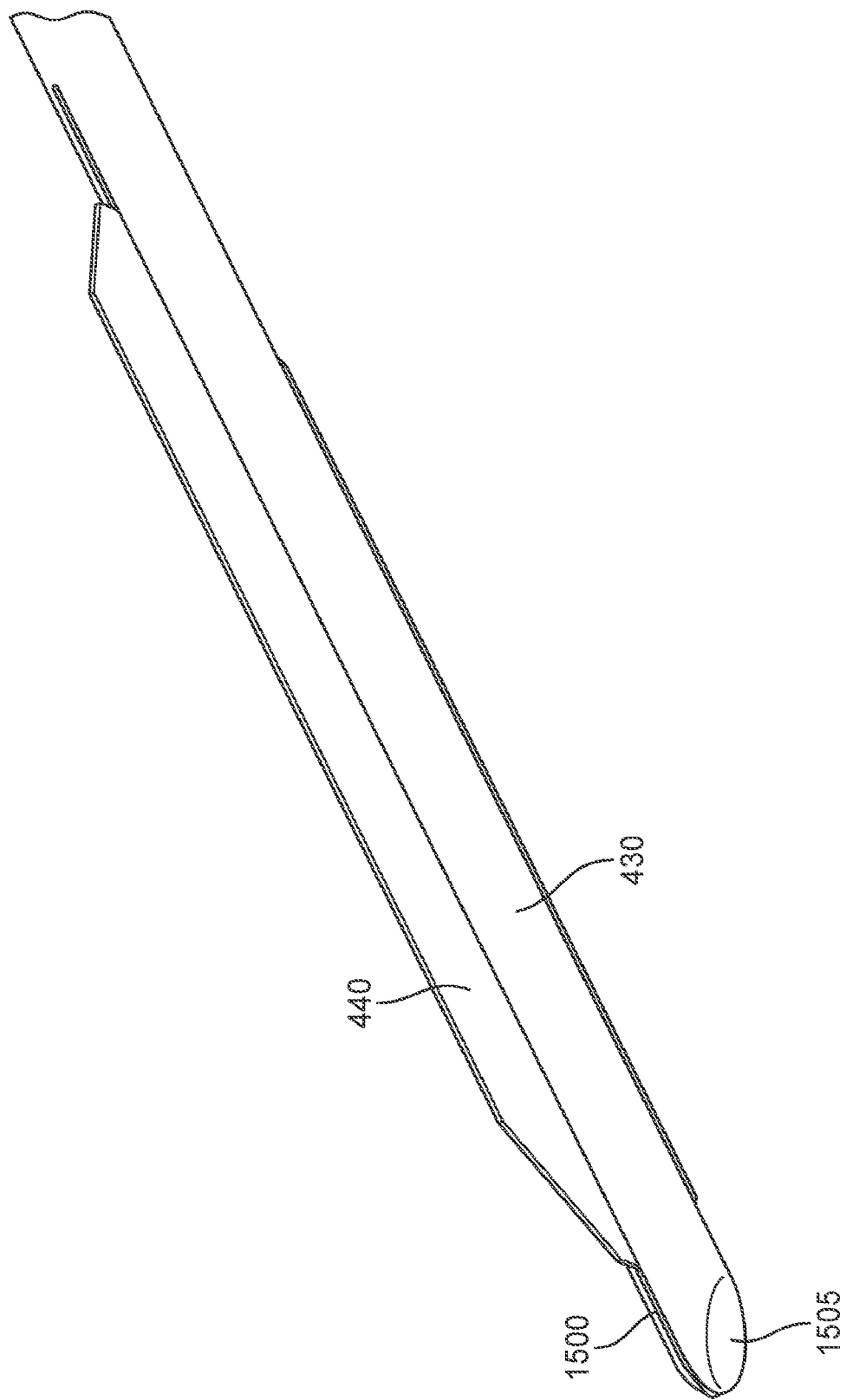
FIG. 15 is a schematic views of an inner shaft and a movable implant supporting flange member held therein.

FIG. 15 is a schematic views of an inner shaft and a movable implant supporting flange member held therein. As shown in FIG. 15, inner shaft 430 may include a slit 1500 in which movable implant supporting flange member 440 is disposed. Movable implant supporting flange member 440 may be snugly fitted within slit 1500 so that movable implant supporting flange member 440 moves when inner shaft 430 is moved. In addition, the distal tip of inner shaft 430 may include a beveled end 1505 in order to facilitate insertion of this distal tip into the recess (445; FIG. 4) at the distal end of outer shaft 390.

Figure 16:
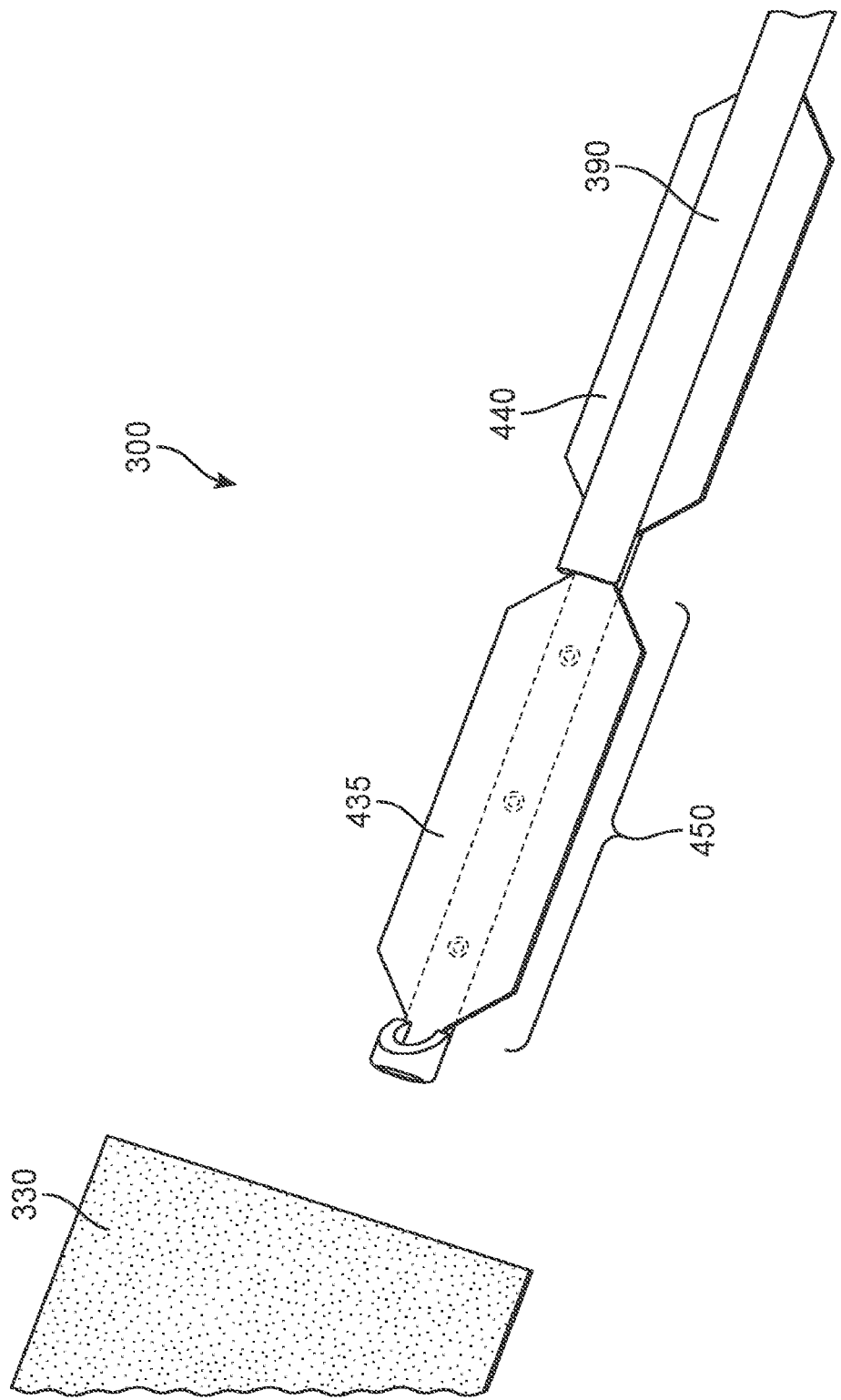
FIG. 16 is a schematic view of the implant holding portion of the implant delivery device with the implant supporting flange member fully withdrawn and with the implant released from the implant delivery device.

In order to fully release the implant from the recess in the outer shaft, the inner shaft is retracted further, completely withdrawing the movable implant supporting flange member from the recess. FIG. 16 is a schematic view of the implant holding portion of the implant delivery device with the implant supporting flange member fully withdrawn and with the implant released from the implant delivery device. A shown in FIG. 16, movable implant supporting flange member 440 has been moved further proximally and no longer overlaps with fixed implant supporting flange member 435. Accordingly, implant 330 is released from recess 450 in outer shaft 390 of implant delivery device 300.

Figure 17:
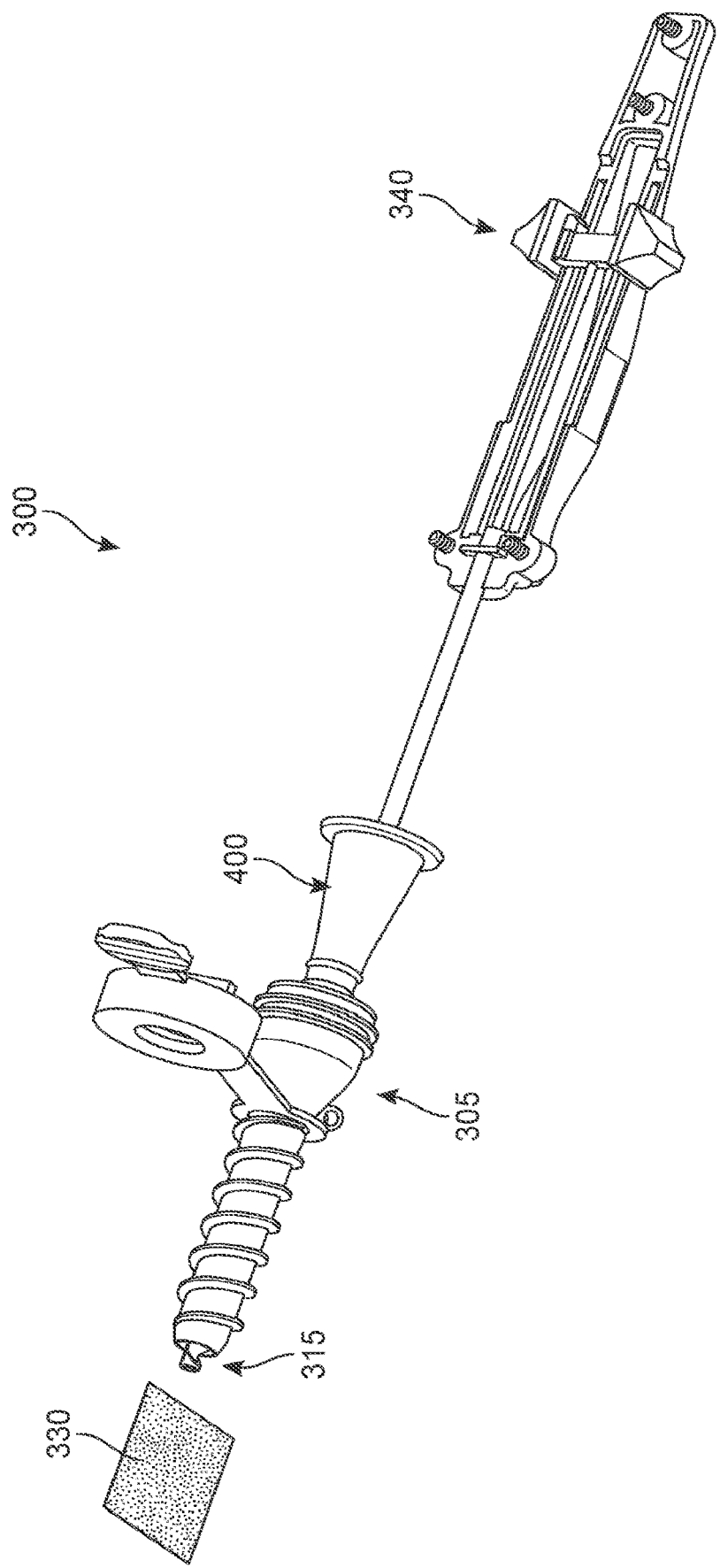
FIG. 17 is a schematic view of the implant delivery device being withdrawn through the cannula after having delivered the implant.

Once implant 330 is secured at the surgical site and released, implant delivery device 300 may be removed from the surgical site through cannula 305. FIG. 17 is a schematic view of implant delivery device 300 being withdrawn through cannula 305 after having delivered implant 330. FIG. 17 further shows slider member 340 in its most proximal location having been slid proximally to fully retract the movable implant supporting flange member (440; FIG. 16). In addition, FIG. 17 also shows cannula sealing member 400 partially withdrawn from cannula 305.

Figure 18:
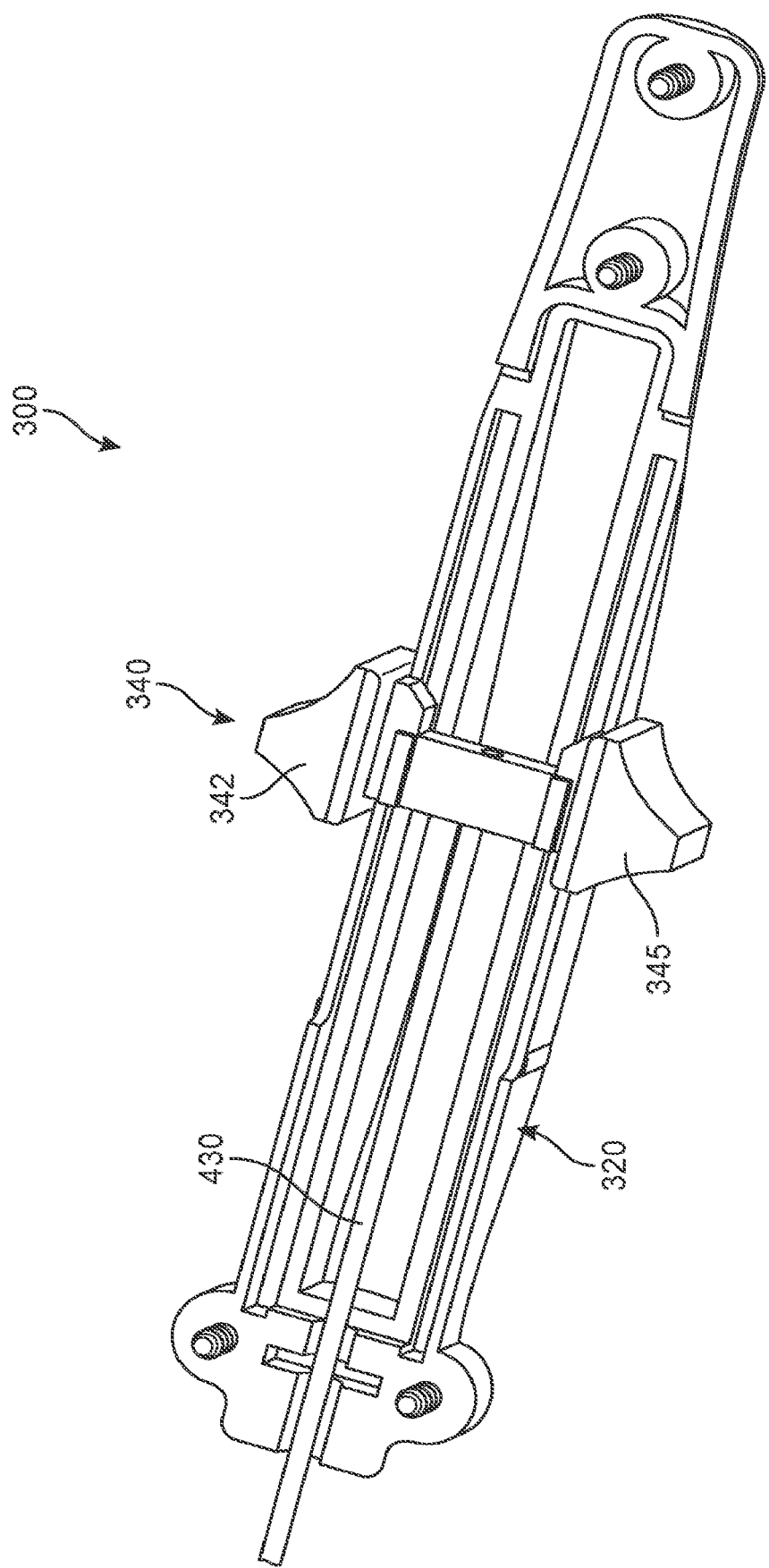
FIG. 18 is a schematic view of the handle of the implant delivery device with an outer panel removed to reveal the inner components of the handle.

FIG. 18 is a schematic view of the handle of the implant delivery device with an outer panel removed to reveal the inner components of the handle. FIG. 18 is included to further illustrate the details of slider member 340 and the attached inner shaft 430.

Figure 19:
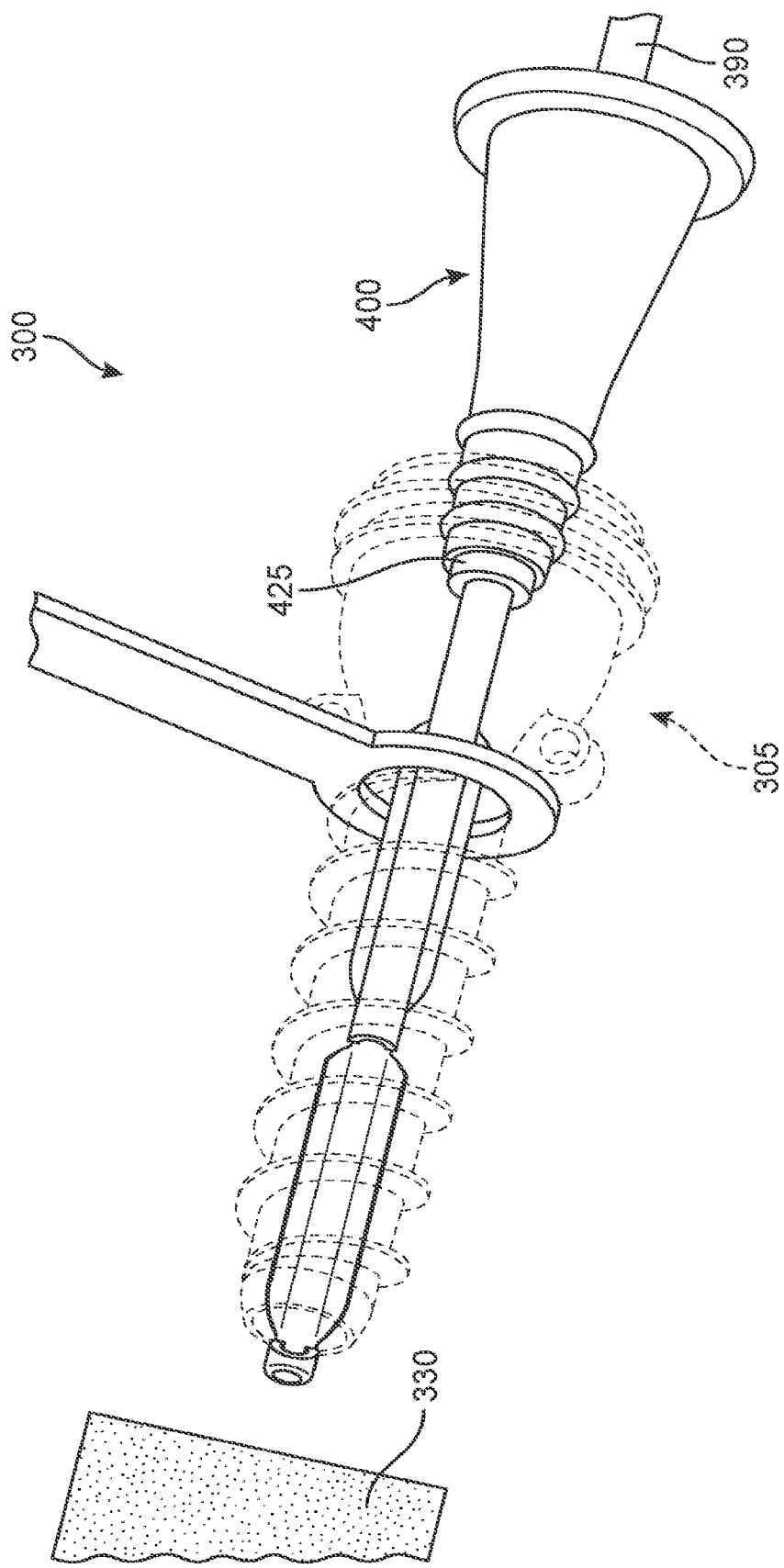
FIG. 19 is a schematic view of the implant delivery device being withdrawn through the cannula with the cannula shown in phantom to reveal the ring on the outer shaft of the implant delivery device pulling the cannula seal member out of the cannula.

FIG. 19 is a schematic view of the implant delivery device being withdrawn through the cannula with the cannula shown in phantom to reveal the ring on the outer shaft of the implant delivery device pulling the cannula seal member out of the cannula. As shown in FIG. 19, ring 425 on outer shaft 390 is abutted against the distal end of cannula sealing member 400. Accordingly, because of the positioning of ring 425, withdrawal of outer shaft 390 through cannula 305 unseats cannula sealing member 400 from cannula, permitting full removal of implant delivery device 300 without cannula sealing member 400 remaining stuck within cannula 305 and sliding off the end of outer shaft 390.

Figure 20:
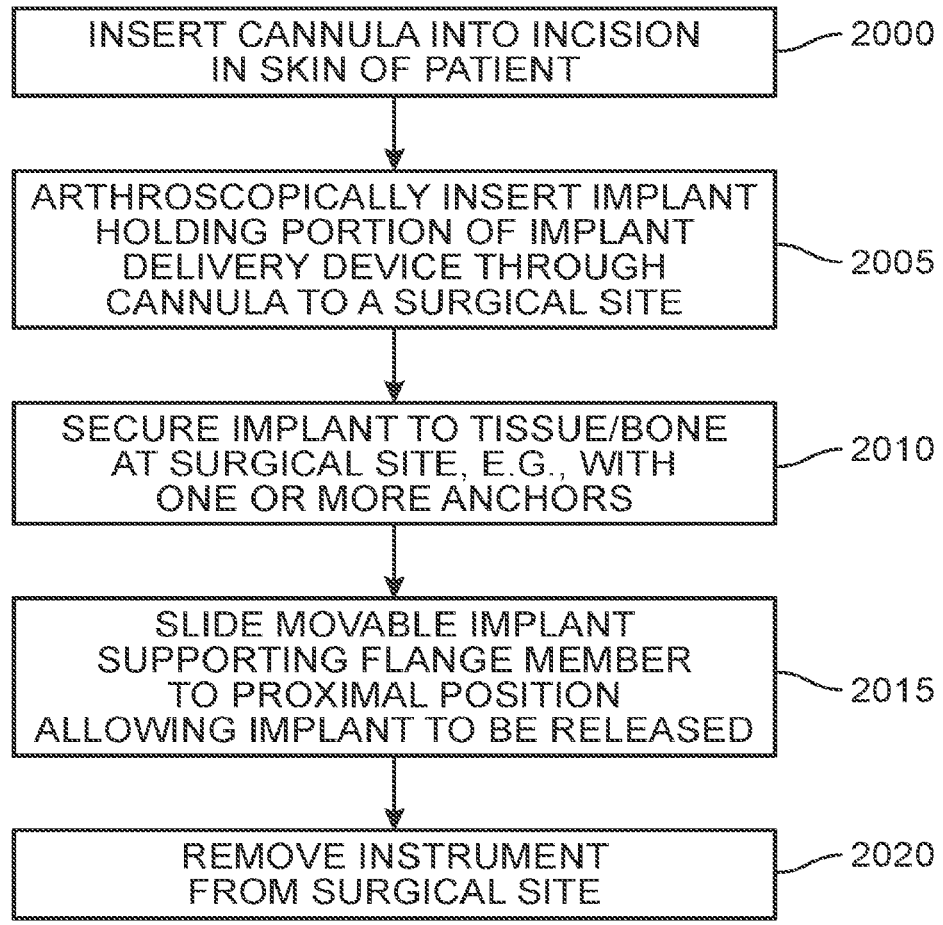
FIG. 20 is a flowchart illustrating a method of delivering a sheet-like implant to a surgical site using the implant delivery device shown and discussed with respect to FIGS. 3-19.

FIG. 20 is a flowchart illustrating a method of delivering a sheet-like implant to a surgical site using the implant delivery device shown and discussed with respect to FIGS. 3-19. As shown in FIG. 20, the method of delivering the implant may include inserting a cannula into an incision in the skin of a patient. (Step 2000.) In some embodiments, the method may include placing a sheet-like implant into the implant holding portion of the implant delivery device. However, in other embodiments, this process of loading the implant into the implant delivery device may be done as a manufacturing step, and the loaded implant delivery device may be provided to the surgeon ready for use.

In addition, once the cannula is inserted, the method may also include arthroscopically inserting the implant holding portion of the implant delivery device through the cannula to a surgical site. (Step 2005.) It will be noted that, in some cases, the implant delivery device may be used in non-arthroscopic (e.g., open) surgeries. It will be further noted that the disclosed implant delivery device need not necessarily be used with a cannula such as cannula 305. If the implant delivery device were to be used during an open surgery, the cannula would not be necessary.

The next step in the method involves the securing of the implant to tissue/bone at the surgical site, for example, with one or more anchors. (Step 2010.) Once the implant has been secured, the movable implant supporting flange member may be moved to the proximal position (by moving the slider member in the proximal direction) allowing the implant to be released. (Step 2015.) Finally, once the implant has been released, the instrument (i.e., the implant delivery device) may be removed from the surgical site. (Step 2020.)

While various embodiments are described, the description is intended to be exemplary, rather than limiting and it will be apparent to those of ordinary skill in the art that many more embodiments and implementations are possible that are within the scope of the disclosed embodiments. Although many possible combinations of features are shown in the accompanying figures and discussed in this detailed description, many other combinations of the disclosed features are possible. Any feature or element of any embodiment may be used in combination with or substituted for any other feature or element in any other embodiment unless specifically restricted. Further, unless otherwise specified, any step in a method or function of a system may take place in any relative order in relation to any other step described herein.

What is claimed is:

1. A method of delivering a sheet-like implant to a surgical site, comprising:
    locating an access cannula and an implant delivery device that is received in the access cannula in an incision in a patient, wherein the implant delivery device includes a movable implant supporting flange member, and wherein a combination of the movable implant supporting flange member and a sheet-like implant that is extending along the movable implant supporting flange member are being held in a constrained condition by an interior of the access cannula;
    advancing the implant delivery device along the interior of the access cannula toward a surgical site until the sheet-like implant and the movable implant supporting flange member have at least partially exited the access cannula and are no longer being held in the constrained condition by the interior of the access cannula;
    anchoring the sheet-like implant to tissue at the surgical site;
    sliding the movable implant supporting flange member at least partially back through the access cannula and past at least part of the sheet-like implant; and
    withdrawing the implant delivery device from the surgical site leaving the sheet-like implant at the surgical site.

2. The method of claim 1, wherein the implant delivery device further includes a fixed implant supporting flange member that extends along and contacts a first side of the sheet-like implant, the movable implant supporting flange member extending along and contacting a second side of the sheet-like implant opposite the first side.

3. The method of claim 2, wherein said sliding moves the movable implant supporting flange member longitudinally relative to the fixed implant supporting flange member.

4. The method of claim 2, wherein the movable implant supporting flange member is attached to a first shaft of the implant delivery device, and the fixed implant supporting flange member is attached to a second shaft of the implant delivery device.

5. The method of claim 4, wherein the first shaft is slidably received in the second shaft.

6. The method of claim 2, wherein the fixed implant supporting flange member and the movable implant supporting flange member are flexible and resilient.

7. A method of delivering a sheet-like implant to a surgical site, comprising:
    positioning a sheet-like implant at a surgical site via an implant delivery device that includes a fixed implant supporting flange member that extends along and contacts a first side of the sheet-like implant at the surgical site and a movable implant supporting flange member that extends along and contacts a second side of the sheet-like implant opposite the first side at the surgical site;
    wherein at least one of the fixed implant supporting flange member and the movable implant supporting flange member is flexible and resilient so as to be collapsible upon delivery through an access cannula;
    anchoring the sheet-like implant to tissue at the surgical site;
    sliding the movable implant supporting flange member in a longitudinal direction relative to the fixed implant supporting flange member at the surgical site such that the movable implant supporting flange member slides past at least part of the sheet-like implant at the surgical site;
    withdrawing the delivery device from the surgical site leaving the sheet-like implant at the surgical site.

8. The method of claim 7 further comprising surgically repairing the tissue with at least one of a suture and an anchor prior to said positioning and said anchoring.

9. The method of claim 7, wherein, prior to said sliding, the movable implant supporting flange member at least partially overlaps the fixed implant supporting flange member on the respective sides of the sheet-like implant.

10. The method of claim 9, wherein, following said sliding, the movable implant supporting flange member no longer overlaps any portion of the fixed implant supporting flange member.

11. The method of claim 7, wherein said sliding moves the movable implant supporting flange member in a proximal direction relative to the fixed implant supporting flange member.

12. The method of claim 7, wherein the movable implant supporting flange member is attached to a first shaft of the implant delivery device, and the fixed implant supporting flange member is attached to a second shaft of the implant delivery device.

13. The method of claim 12, wherein the second shaft extends from a handle of the implant delivery device to a distal end of the implant delivery device, the handle including a slider member connected to the first shaft, wherein said sliding includes moving the slider member in a proximal direction away from the distal end of the implant delivery device.

14. The method of claim 13, wherein the first shaft connects the slider member to the movable implant supporting flange member.

15. The method of claim 12 wherein the second shaft includes a distal recess into which a distal tip of the first shaft is received prior to said sliding, and wherein the distal tip exits the distal recess during said sliding.

16. The method of claim 12, wherein the first shaft is slidably received in the second shaft.

17. The method of claim 16, wherein the second shaft includes a slot into which the movable implant supporting flange member is received during said sliding.

18. The method of claim 7, wherein the sheet-like implant includes a sheet thickness that extends between the first side of the sheet-like implant and the second side of the sheet-like implant.

\* \* \* \* \*